United States Patent [19]
Ito

[11] Patent Number: 6,087,147
[45] Date of Patent: Jul. 11, 2000

[54] α-AMYLASE GENE HAVING ABILITY FOR HIGHLY PRODUCING MALTOPENTAOSE, VECTOR CONTAINING SAID GENE AND TRANSFORMANT

[75] Inventor: Yoshifumi Ito, Tsukuba, Japan

[73] Assignee: Director of National Food Research Institute, Ministry of Agriculture, Forestry and Fisheries, Tsukuba, Japan

[21] Appl. No.: 09/017,706

[22] Filed: Feb. 5, 1998

[30] Foreign Application Priority Data

Oct. 21, 1997 [JP] Japan ................................. 9-305071

[51] Int. Cl.⁷ ............................. C12W 9/28; C12W 1/20; C07H 21/04; C12N 9/28; C12N 1/20; C12N 15/00
[52] U.S. Cl. ................. 435/202; 435/252.33; 435/320.1; 536/23.2
[58] Field of Search ................. 435/202, 320.1, 435/252.33; 536/23.2

[56] References Cited

U.S. PATENT DOCUMENTS 5,204,254  4/1993  Schmid et al. .......................... 435/202
5,304,723  4/1994  Schmid et al. ........................ 435/252.1

OTHER PUBLICATIONS

Rudinger (Jun. 1976) Characteristics of the amino acids as components of a peptide hormone sequence. In: Peptide Hormones. Ed. J. A. Parsons. University Park Press, Baltimore, MD. pp. 1–7.

Ngo et al. (Jan. 1994) Computational complexity, protein structure prediction, and the ILevinthal paradox. In: The Protein Folding Problem and Tertiary Structure Prediction. Eds. Merz et al. Birkhauser et al. Boston, MA. pp. 491–495.

Thornton et al. (Sep. 1995) Protein Engineering: Editorial Overview. Current Opinion in Biotechnology 6(4): 367–369.

Wallace (Apr. 1993) Understanding cytochrome c function: engineering protein structure by semisynthesis. The FASEB Journal 7: 505–515.

Osamu Shida, et al., Biosci. Biotech. Biochem., vol. 56, No. 1, pp. 76–80, "Cloning and Nucleotide Sequence of the Maltopentaose–Forming Amylase Gene from Pseudomonas SP. KO–8940", 1992.

Hisashi Okemoto, et al., Applied Microbiology and Biotechnology, vol. 25, pp. 137–142, "Isolation and Cultivation of a Novel Microorganism Producing a Maltopentaose–Forming Enzyme", 1986.

*Primary Examiner*—Karen Cochrane Carlson
*Assistant Examiner*—Einar Stole
*Attorney, Agent, or Firm*—Oblon, Spivak, McClelland, Maier & Neustadt, P.C.

[57] ABSTRACT

A modified enzyme having a reduced maltopentaose decomposing activity and improvements in practical usability was provided by a gene coding for α-amylase highly producing maltopentaose, the α-amylase comprising an amino acid sequence where an amino acid residue at 57- or 139-position has been substituted in the amino acid sequence of maltopentaose-forming amylase derived from Pseudomonas sp. KO-8940 (Shida, O. et al., Biosci. Biotech. Biochem. Vol. 56, 76–80 (1992)).

30 Claims, 7 Drawing Sheets

G5  G3  G2

G5  G3  G2

G5 G3 G2

G5 G3 G2

α-AMYLASE GENE HAVING ABILITY FOR HIGHLY PRODUCING MALTOPENTAOSE, VECTOR CONTAINING SAID GENE AND TRANSFORMANT

FIELD OF THE INVENTION

The present invention relates to a gene coding for maltopentaose-forming α-amylase used for producing maltopentaose, a plasmid vector containing the same and transformant containing said plasmid vector.

The maltopentaose-forming α-amylase is an enzyme which produces maltopentaose, i.e. consisting of 5 glucose molecules by hydrolyzing α-1,4-glycoside linkages of polysaccharides such as starch, amylose etc. composed of glucose molecules bound to one another via α-1,4-glycoside linkages. By use of this enzyme, maltopentaose can be produced from starch.

The present invention relates to a gene coding for maltopentaose-forming α-amylase, a plasmid vector containing said gene and transformant. Said enzyme is derived from microorganism belonging to the genus Pseudomonas and is utilizable for producing maltopentaose from starting materials such as starch etc. According to the present invention, said enzyme has been improved by genetic engineering means to achieve improvements in practical use.

BACKGROUND OF THE INVENTION

Maltopentaose-forming α-amylase derived from microorganisms belonging to the genus Pseudomonas can be used to enzymatically produce maltopentaose from starch etc.

However, said enzyme has an additional activity of decomposing the resulting maltopentaose into maltotriose and maltose. Accordingly, decomposition of the formed maltopentaose does also proceed with time to reduce the yield of maltopentaose and to simultaneously generate maltotriose and maltose as by-products. Therefore, it was difficult to produce maltopentaose efficiently by use of said enzyme.

An object of the present invention is to develop an improved enzyme, which has an enhansed practical usability, by modification to the gene of said enzyme to reduce the activity of decomposing maltopentaose.

SUMMARY OF THE INVENTION

The present inventors planed protein engineering study for conversion of amino acid residues participating in binding to a substrate of maltopentaose-forming α-amylase derived from microorganism belonging to the genus Pseudomonas with other amino acids, and by modifying the gene of said enzyme, they succeeded in production of said enzyme excellent in practical usability to arrive at the present invention.

That is, the present invention according to claim 1 is a gene coding for α-amylase having ability for highly producing maltopentaose, comprising an amino acid sequence where an amino acid residue at 57- or 139-position has been substituted in the amino acid sequence of maltopentaose-forming α-amylase derived from Pseudomonas sp. KO-8940 (Shida, O. et al., Biosci. Biotech. Biochem., Vol. 56, 76–80 (1992)).

The present invention according to claim 2 is a plasmid containing the gene as described in claim 1.

The present invention according to claim 3 is a plasmid according to claim 2, wherein the plasmid has any one of the amino acid sequences as shown in SEQ ID NOS: 3 to 8 in the Sequence Listing.

The present invention according to claim 4 is transformed Escherichia coli (FERM BP-6116) carrying a plasmid having the amino acid sequence as shown in SEQ ID NO:3 in the Sequence Listing.

The present invention according to claim 5 is transformed Escherichia coli (FERM BP-6119) carrying a plasmid having the amino acid sequence as shown in SEQ ID NO:4 in the Sequence Listing.

The present invention according to claim 6 is transformed Escherichia coli (FERM BP-6115) carrying a plasmid having the amino acid sequence as shown in SEQ ID NO:5 in the Sequence Listing.

The present invention according to claim 7 is transformed Escherichia coli (FERM BP-6117) carrying a plasmid having the amino acid sequence as shown in SEQ ID NO:6 in the Sequence Listing.

The present invention according to claim 8 is transformed Escherichia coli (FERM BP-6118) carrying a plasmid having the amino acid sequence as shown in SEQ ID NO:7 in the Sequence Listing.

The present invention according to claim 9 is transformed Escherichia coli (FERM BP-6114) carrying a plasmid having the amino acid sequence as shown in SEQ ID NO:8 in the Sequence Listing.

Figure 1:
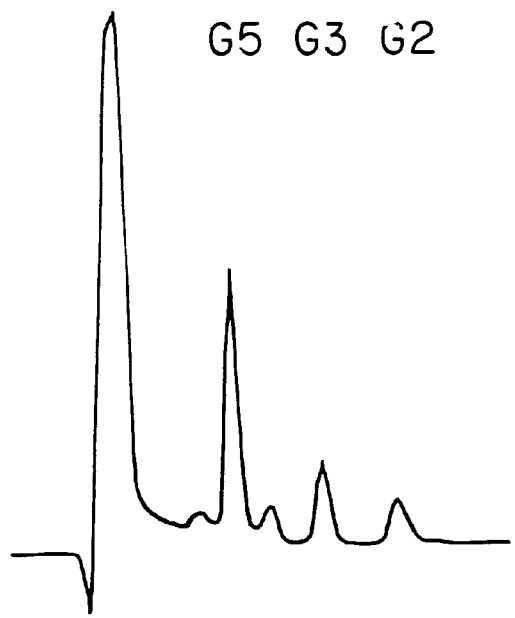
FIG. 1 shows the soluble starch decomposing activity 30 minutes after initiation of treatment, of the wild-type enzyme obtained from wild-type Pseudomonas sp. pOS3410.
Figure 2:
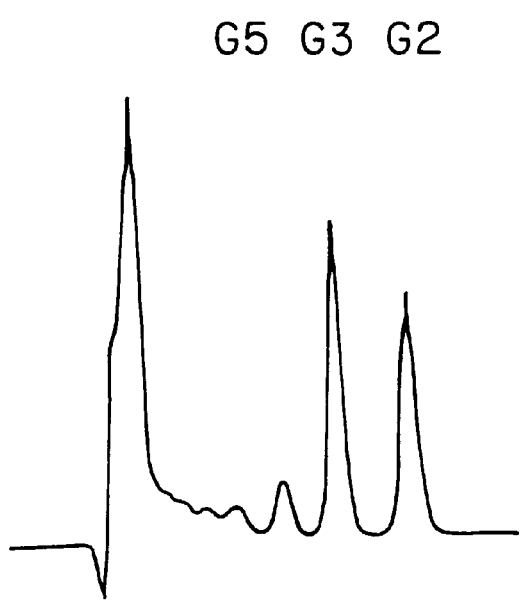
FIG. 2 shows the soluble starch decomposing activity 180 minutes after initiation of treatment, of the wild-type enzyme obtained from wide-type Pseudomonas sp. pOS3410.
Figure 3:
FIG. 3 shows the soluble starch decomposing activity 30 minutes after initiation of treatment, of α-amylase highly producing maltopentaose obtained from the transformed E. coli pOS3410F57 of the present invention.
Figure 4:
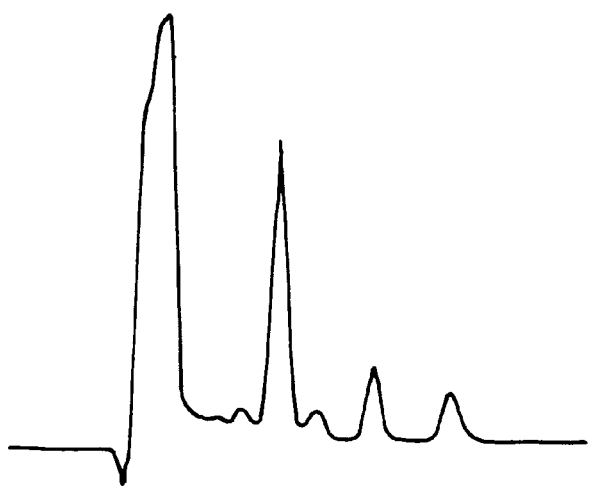
FIG. 4 shows the soluble starch decomposing activity 180 minutes after initiation of treatment. of α-amylase highly producing maltopentaose obtained from the transformed E. coli pOS3410F57 of the present invention.
Figure 5:
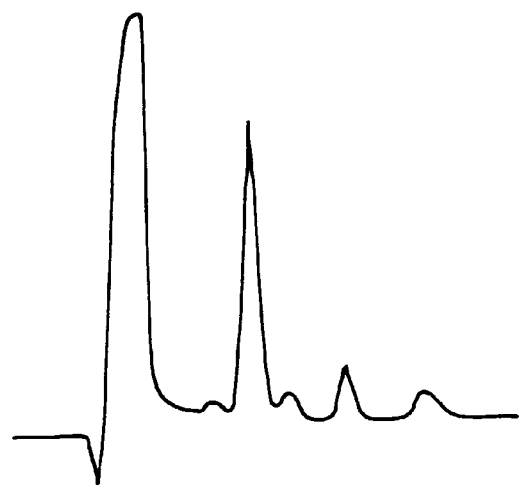
FIG. 5 shows the soluble starch decomposing activity 30 minutes after initiation of treatment, of α-amylase highly producing maltopentaose obtained from the transformed E. coli pOS3410H57 of the present invention.
Figure 6:
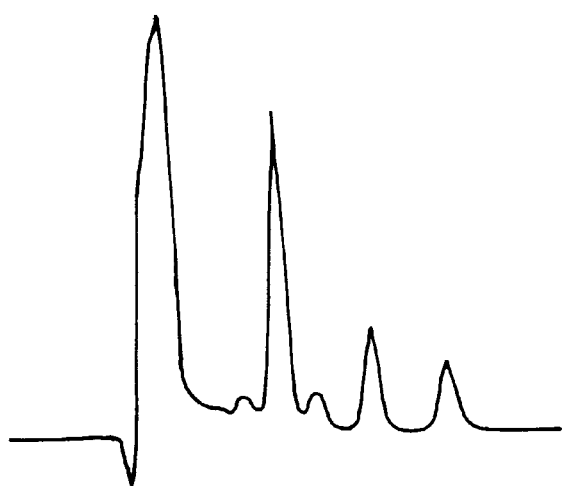
FIG. 6 shows the soluble starch decomposing activity 180 minutes after initiation of treatment, of α-amylase highly producing maltopentaose obtained from the transformed E. coli pOS3410H57 of the present invention.
Figure 7:
FIG. 7 shows the soluble starch decomposing activity 30 minutes after initiation of treatment, of α-amylase highly producing maltopentaose obtained from the transformed E. coli pOS3410L57 of the present invention.
Figure 8:
FIG. 8 shows the soluble starch decomposing activity 180 minutes after initiation of treatment, of α-amylase highly producing maltopentaose obtained from the transformed E. coli pOS3410L57 of the present invention.
Figure 9:
FIG. 9 shows the soluble starch decomposing activity 30 minutes after initiation of treatment, of α-amylase highly producing maltopentaose obtained from the transformed E. coli pOS3410F139 of the present invention.
Figure 10:
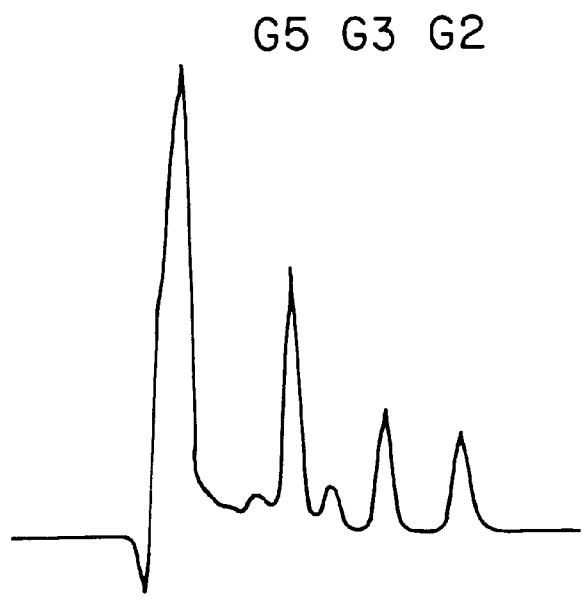
FIG. 10 shows the soluble starch decomposing activity 180 minutes after initiation of treatment, of α-amylase highly producing maltopentaose obtained from the transformed E. coli pOS3410F139 of the present invention.
Figure 11:
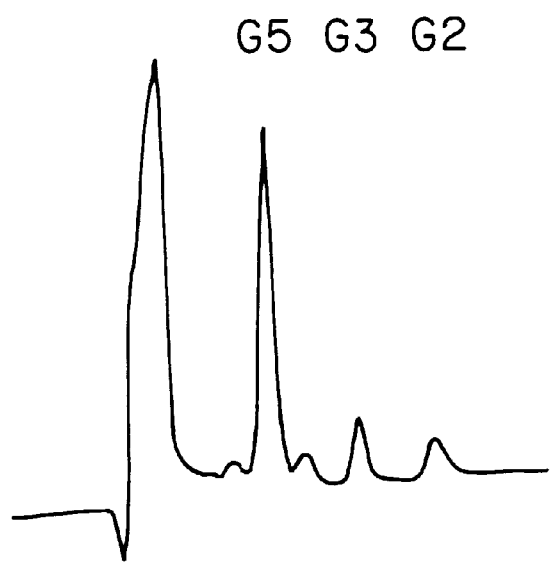
FIG. 11 shows the soluble starch decomposing activity 30 minutes after initiation of treatment, of α-amylase highly producing maltopentaose obtained from the transformed E. coli pOS3410H139 of the present invention.
Figure 12:
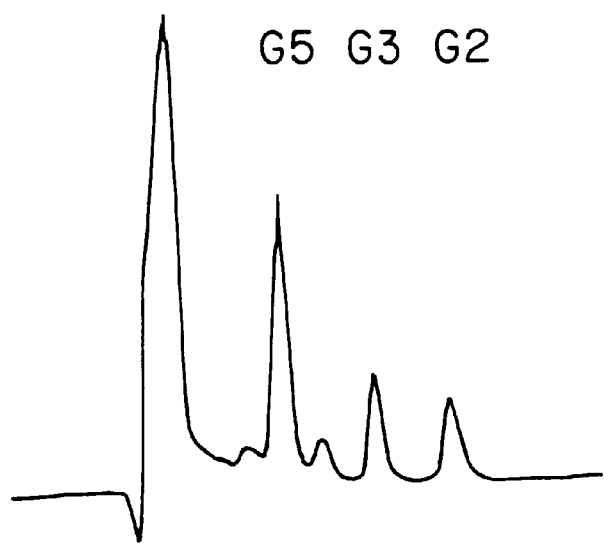
FIG. 12 shows the soluble starch decomposing activity 180 minutes after initiation of treatment, of α-amylase highly producing maltopentaose obtained from the transformed E. coli pOS3410H139 of the present invention.

In the figures, G5 shows the amount of maltopentaose detected; G3 shows the amount of maltotriose detected; and G2 shows the amount of maltose detected

DETAILED DESCRIPTION OF THE INVENTION

By specifically mutating a gene of maltopentaose-forming α-amylase derived from microorganism belonging to the genus Pseudomonas, the present inventors created a series of mutant enzymes with a reduction in the maltopentaose decomposing activity possessed by said enzyme.

The outline of the method is as follows: First, a specific amino acid residue conserved in various α-amylases and involved in binding to a substrate was estimated. The codon of this specific amino acid residue was replaced by another by site-specific mutagenesis to create a mutant gene which produces the enzyme having decreased affinity for maltopentaose. By a transformant obtained by introducing a plasmid containing this mutant gene into E. coli, maltopentaose-forming α-amylase with a reduction in the maltopentaose decomposing activity was produced.

Because such modified enzymes have a decreased activity of decomposing maltopentaose, maltopentaose can be produced from starch etc. in high yield. Simultaneously, the yields of maltose and maltotriose as by-products are very low as compared with those of the wild-type enzyme. That is, said mutant enzyme is superior to the wild-type enzyme in respect of the ability to produce maltopentaose from starch as the starting material.

Hereinafter, the present invention is described in detail.

As described above, the maltopentaose-forming α-amylase gene of the present invention is derived from microorganism belonging to the genus Pseudomonas having the ability to produce maltopentaose-forming α-amylase.

Such microorganism belonging to the genus Pseudomonas having the ability to produce maltopentaose-forming α-amylase include Pseudomonas sp. KO-8940.

The maltopentaose-forming α-amylase can be obtained from said microorganism, specifically by culturing said microorganism in a nutrient medium in a usual manner and then separating the microorganism from the culture. Thereafter, the microorganism is disrupted and centrifuged in a usual manner to give a fraction of maltopentaose-forming α-amylase. Then, purification means such as column chromatography, FPLC, HPLC etc. can be used to prepare highly purified maltopentaose-forming α-amylase.

The amino acid sequence of maltopentaose-forming α-amylase derived from Pseudomonas sp. KO-8940 has already been determined (Shida, O., Kadowaki, K. and Kobayashi, S., Biosci. Biotech. Biochem., Vol. 56, 76–80, (1992)).

The amino acid sequence of this maltopentaose-forming α-amylase was analyzed to identify a portion participating in hydrolysis of α-1, 4-linkages between glucose molecules in a starch molecule and a portion participating in binding to starch.

That is, the amino acid sequence of maltopentaose-forming α-amylase was compared with the amino acid sequences of other amylases, specifically with the amino acid sequence of Taka-amylase (Tsukagoshi, N., Furukawa, M., Nagaba, H., Kirita, N., Tsuboi, A. and Udaka, S., Gene, Vol. 84 (1989)) and with the amino acid sequence of maltotetraose-forming α-amylase (Fujita, M., Trigoe, K., Nakada, U., Tsuzuki, K., Kubota, M. and Tsujikawa, Y. J. Bacteriol., Vol. 171, 1333–1339 (1989)).

The amino acid sequences of said enzyme, Taka-amylase and maltotetraose-forming α-amylase were aligned with one another using a homology analysis program "Clustal W". As a result of X-ray crystal analysis, it was found that amino acid residues in Taka-amylase (Matsuura, Y. et al., J. Biochem. Vol. 95, 697–702 (1984)) and in maltotetraose-forming α-amylase (Morisita, Y. et al., J. Mol. Biol. Vol. 267, 661–672 (1997)), whose residues having already been revealed to participate in hydrolysis and binding to a substrate, were present in common at almost the same positions in each amino acid sequence of these three enzymes.

According to this result, candidates for amino acid residues which can be replaced without affecting the enzyme activity and can reduce the strength of binding to maltopentaose were identified to be a tryptophan residue at the 57-position and a tyrosine residue at the 139-position located apart from the active site involved directly in hydrolysis. That is, these amino acid residues are amino acid residues involved in binding to glucose molecules in a starch molecule.

Then, the method of converting both of the amino acid residues into other amino acid residues was examined.

The conversion of the amino acid residues can be carried out for example in the following manner.

First, two oligonucleotides for converting both of the amino acid residues into other amino acid residues were synthesized using a phosphoamidide reagent in a DNA synthesizer (Applied Biosystems). Out of the two oligonucleotides, one for converting a tryptophan residue at the 57-position was designated oligonucleotide A, and another for converting a tyrosine residue at the 139-position was designated oligonucteotide B.

The nucleotide sequences of oligonucleotides A and B are shown in SEQ ID NOS: 1 and 2 respectively.

Separately, a 530 bp EcoRI-PstI fragment containing a DNA region for nucleotide substitution was prepared from pOS3410. This fragment was inserted into an EcoRI-PstI site in phage vector M13tv18 whereby M13tv18-A1 was constructed.

Site-specific mutagenesis can be carried out using e.g. Sculptor™ In Vitro Mutagenesis Kit (Amershanm.

If Sculptor In Vitro Mutagenesis Kit is to be used, site-specific mutagenesis is carried out according to the Experimental Instructions of Amersham That is, oligonucleotides A and B were annealed to a single-stranded DNA of M13tv18-A1 as the template and subjected to elongation and ligation by T7 polymerase and T4DNA ligase in the presence of dCTP αS, dATP, dGTP, dTTP and ATP.

After un-reacting molecules with single-stranded chains are cleaved with treatment with T5 exonuclease, the DNA chain of the template is cleaved with restriction enzyme NciI. Further, the DNA chain of the template is completely digested with exonuclease III.

The single-stranded DNA thus synthesized is transformed into E. coli. Whether or not this single-stranded DNA has the nucleotide substitution can be confirmed by preparing the single-stranded DNA from the transformant and analyzing its nucleotide sequence.

A tryptophan residue at the 57-position and a tyrosine residue at the 139-position in the amino acid sequence of said enzyme can be converted according to the above method. For this conversion, use can also be made of the PCR method (Gene Amplification (PCR) Method, "Tanpa-kusitsu Kakusan Koso" (Protein, Nucleic Acid, and Enzyme), ed. Kaoru Fujinaga, Vol. 35, No. 17 (1990), published by Kyoritsu Shuppan K. K.).

That is, the two amino acid residues can be converted by conducting 2-stage PCR using oligonucleotide A containing the nucleotide substitution as shown in SEQ ID NO:1 and oligonucleotide B containing the nucleotide substitution as shown in SEQ ID NO:2, as well as oligonucleotides complementary thereto.

From the recombinant DNA thus mutated, the EcoRI-PstI fragment is recovered. This EcoRI-PstI fragment is used to substitute for its corresponding DNA fragment in pOS3410, using a DNA ligation kit (Takara Shuzo Co., Ltd.). As a result, it is possible to produce six plasmids producing mutant maltopentaose-forming α-amylases with alternations in the amino acid sequence.

The six plasmids were designated pOS3410F57, pOS3410H57, pOS3410L57, pOS3410F139, pOS3410H139 and pOS3410L139 respectively, and their nucleotide sequences and the amino acid sequences of enzymes corded by said nucleotide sequence are as shown in SEQ ID NOS:3, 4, 5, 6, 7 and 8 in the Sequence Listing.

Among these six plasmids, pOS3410F57, pOS3410H57 and pOS3410L57 can produce the amino acid sequences of α-amylases highly producing maltopentaose, where tryptophan at the 57-position has been replaced by phenylalanine, histidine and leucine respectively in the amino acid sequence of the wild-type, maltopentaose-producing amylase.

Further, pOS3410F139, pOS3410H139 and pOS3410L139 can produce the amino acid sequences of α-amylases highly producing maltopentaose, where tryptophan at the 139-position has been replaced by phenylalanine, histidine and leucine respectively in the amino acid sequence of the wild-type, maltopentaose-producing α-amylase.

Transformation of these plasmid DNAs into E. coli can be effected according to e.g. the calcium chloride method of Cohen et al. (Proc. Natl. Acad. Sci. USA, 69: 2110–2114 (1972)).

That is, E. coli is cultured in 50 ml LB medium and harvested by centrifugation at the early logarithmic growth phase. The microorganism is suspended in ice-cold 0.1 M magnesium chloride in 25 ml of the medium and harvested by centrifugation. The harvested microorganism is suspended in ice-cold 0.1 M calcium chloride in 12.5 ml of the medium and maintained on ice for 30 minutes. The microorganism is harvested by centrifugation and then suspended in 2 ml of the same solution. 10 µl TE buffer containing 10 ng plasmid DNA is added to 200 µl of the bacterial solution, and the mixture is maintained on ice for 45 minutes. It is heated at 42° C. for 1 minute, and 1 ml LB medium is added and gently shaken at 37° C. for 1 hour. An aliquot of the culture is plated onto an LB agar medium containing 100 µg/ml ampicillin and cultured at 37° C. overnight, from which the target transformant is selected.

Transformation of the plasmid DNA into E. coli can also be effected according to the electroporation method ("Shin-Kiso Seikagaku Jikkenho 7" (New Fundamental Experimental Method 7 in Biochemistry), Genetic Engineering, ed. K. Miura et al. published in 1988 by Maruzen K. K.).

The resulting E. coli transformants have been deposited with the National Institute of Bioscience and Human-Technology, Agency of Industrial Science and Technology, Ministry of International Trade and Industry, 1–3, Higashi 1-chome, Tsukuba-shi, Ibaraki-ken 305, Japan, and their accession numbers in the order of the introduced plasmids pOS3410F57, pOS3410H57, pOS3410L57, pOS3410F139, pOS3410H139 and pOS3410L139 are FERM BP-6116, FERM BP-6119, FERM BP-6115, FERM BP-6117, FERM BP-6118 and FERM BP-6114 respectively.

The α-amylase highly producing maltopentaose, produced by these transformants, can efficiently produce maltopentaose because although it decomposes α-1,4-linkages between glucose molecules in starch, its activity of decomposing α-1,4-linkages in the formed maltopentaose is low.

When the enzyme obtained from the present gene of α-amylase highly producing maltopentaose is used, maltopentaose can be obtained in high yield due to the reduction of decomposition of maltopentaose formed by reacting said enzyme to starch etc.

The amino acids shown in SEQ ID NO: 3, 4, 5, 6, 7 and 8 are separately listed in the Sequence Listing as SEQ ID NO: 9, 10, 11, 12, 13 and 14, respectively.

EXAMPLE

Hereinafter, the present invention is described in more detail with reference to the Examples, which are not intended to limit the scope of the present invention.

Example 1

By comparison of the amino acid sequence of maltopentaose-forming α-amylase derived from Pseudomonas sp. KO-8940 (Shida, O., Kadowaki, K. and Kobayashi, S., Biosci. Biotech. Biochem., Vol. 56, 76–80 (1992)) with the amino acid sequences of Taka-amylase (Tsukagoshi, N., Furukawa, M., Nagaba, H., Kirita, N., Tsuboi, A. and Udaka, S., Gene, Vol. 84 (1989)) and of maltotetraose-forming α-amylase (Fujita, M., Trigoe, K., Nakada. U., Tsuzuki, K., Kubota. M. and Tsujikawa, Y. J. Bacterial., Vol. 171, 1333–1339 (1989)), a tryptophan residue at the 57-position and a tyrosine residue at the 139-position in said enzyme were estimated to be amino acid residues involved in binding to glucose in a starch molecule as the substrate.

Oligonucleotide A (SEQ ID NO:1 in the Sequence Listing) and oligonucleotide B (SEQ ID NO:2 in the Sequence Listing) for converting both of the amino acid residues into other amino acid residues were synthesized using a phosphoamidide reagent in a DNA synthesizer (Applied Biosystems).

Separately, a 530 bp EcoRI-PstI fragment containing a DNA region for nucleotide substitution was prepared from pOS3410 and inserted into an EcoRI-PstI site in phage vector M13tv18 whereby M13tv18-A1 was prepared.

Site-specific mutagenesis was carried out using Sculptor In Vitro Mutagenesis Kit (Amersham), where the procedure followed the Experimental Instructions of Amersham.

That is, oligonicleotides A and B were annealed to a single-stranded DNA of M13tv18-A1 as the template and subjected to elongation and ligation by T7 polymerase and T4DNA ligase in the presence of dCTP αS, DATP, dGTP, dTTP and ATP.

Then, un-reacting molecules with single-stranded chains were cleaved with treatment with T5 exonuclease, and the DNA chain of the template was cleaved with restriction enzyme NciI. Further, the DNA chain of the template was completely digested with exonuclease III, and the synthesized single-stranded DNA having the nucleotide substitution was transformed into E. coli.

The single-stranded DNA was prepared from the resulting transformant, then sequenced using Dye Primer cycle sequencing kit (Applied Biosystems) and analyzed for its DNA sequence by a DNA sequencer (Applied Biosystems, Model 373).

The EcoRI-PstI fragment was recovered from the recombinant DNA whose mutation was thus confirmed, and it was used to substitute for its corresponding DNA fragment in pOS3410, using a DNA ligation kit (Takara Shuzo Co., Ltd.), thereby producing plasmids, i.e. pOS3410F57, pOS3410H57, pOS3410L57, pOS3410F139, pOS3410H139 and pOS3410L139 (see SEQ ID NOS: 3, 4, 5, 6, 7 and 8 in the Sequence Listing), which produce alternations in the amino acid sequence to produce α-amylase highly producing maltopentaose.

Further, these plasmid DNAs were transformed into E. coli according to the calcium chloride method of Cohen et al. (Proc. Natl. Acad. Sci. USA, 69: 2110–2114 (1972)).

The resulting E. coli transformants have been deposited with the National Institute of Bioscience and Human-Technology, Agency of Industrial Science and Technology, Japan, and their accession numbers are FERM BP-6116, FERM BP-6119, FERM BP-6115, FERM BP-6117, FERM BP-6118 and FERM BP-6114 respectively.

Separately, the wild-type enzyme obtained from usual Pseudomonas sp. pOS3410 and its mutant enzyme i.e. α-amylase highly producing maltopentaose were prepared according to the method of Shida et al. (Biosci. Biotech. Biochem., 56: 76–80 (1992)).

That is, E. coli carrying a plasmid containing genes for the wild-type and mutant enzymes was cultured at 30° C. in LB medium (Sambrook, J. et al., Molecular Cloning, 2nd edition, 1989, Cold Spring Harbor Laboratory Press). When the absorbance of the culture at 660 nm reached 0.5, isopropyl-β-thiogalactopyranoside (IPTG) was added thereto at a final concentration of 0.1 mM, and the microorganism was cultured for additional 40 hours.

After culture was finished, the microorganism was harvested by centrifugation and its periplasm fraction was prepared by an osmotic shock method to prepare an enzyme specimen. The osmotic shock method is a method in which cells are suspended in a hypertonic solution containing 0.5 M sucrose to be separated from the protoplasm followed by being suspended in a hypotonic. sucrose-free solution so that the cells are rapidly swollen to permit the protein located between the cell wall and cytoplasmic membrane (i.e. in periplasm) to be specifically released out of the cells.

Then, these enzymes were examined for their enzyme activity using soluble starch as a substrate in the following manner.

Soluble starch was treated with 0.25 U of each enzyme and an aliquot of the reaction solution was recovered with time. The reaction solution was diluted 10-fold with water, and 10 μl was subjected to high performance liquid chromatography (LC-6A, manufactured by Shimadzu Corporation) equipped with MCI-GEL CK045 column (10× 200 nm; Mitsubishi Kagaku K. K.). The sample was eluted with distilled water at a temperature of 85° C. under a pressure of 0.3 kg/cm$^2$ at a flow rate of 0.4 ml/min. The reactant was detected by measuring the absorbance at 210 nm with an UV detector (SPD-6A, manufactured by Shimadzu Corporation). The product was identified on the basis of the retention times of standard samples of maltopentaose, maltotriose, and maltose.

The results of detection (absorbance at 210 nm) of the enzyme activities of the respective enzymes after 30- and 180-minute reaction are shown in FIGS. 1 to 14.

Comparison of FIGS. 1 to 14 revealed the following.

First, the wild-type enzyme decomposes (as high as) about 50% of the product maltopentaose 180 minutes later (FIG. 2), as compared with 30 minutes later (FIG. 1). On the other hand, the enzymes derived from plasmid pOS3410F57 (In FIGS. 3 and 4, smaller number shows the results after 30 minutes. This designation applies hereinafter), from pOS3410H57 (FIGS. 5 and 6), and from pOS3410L57 (FIGS. 7 and 8) decomposed 10% or less of maltopentaose even after 180 minutes.

Further, even 360 minutes later when almost 100% of maltopentaose was decomposed by the wild-type enzyme, 50% maltopentaose was not decomposed by the mutant enzymes.

Figure 13:
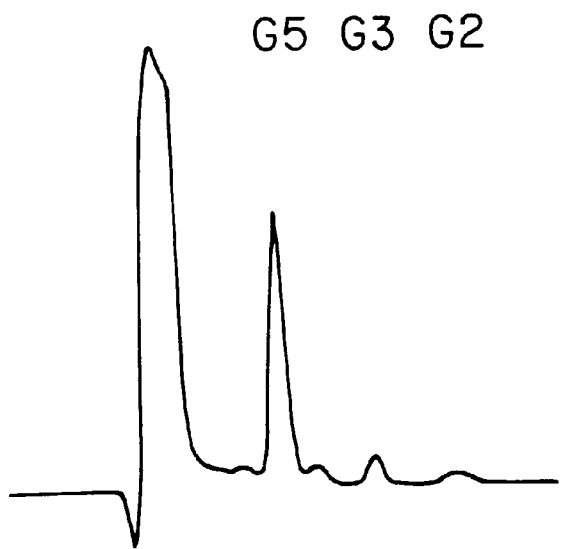
FIG. 13 shows the soluble starch decomposing activity 30 minutes after initiation of treatment, of α-amylase highly producing maltopentaose obtained from the transformed E. coli pOS3410L139 of the present invention.
Figure 14:
FIG. 14 shows the soluble starch decomposing activity 180 minutes after initiation of treatment, of α-amylase highly producing maltopentaose obtained from the transformed E. coli pOS3410L139 of the present invention.

Similar results were also obtained even using the mutant enzymes derived from plasmid pOS3410F139 (FIGS. 9 and 10), pOS3410H139 (FIGS. 11 and 12) and pOS3410L139 (FIGS. 13 and 14).

From this result, it was made evident that the maltopentaose decomposing activity of the mutant enzyme obtained using the plasmid of the present invention, that is, of α-amylase highly producing maltopentaose, is reduced to 20% or less of that of the wild-type enzyme, so maltopentaose is not decreased even if the enzyme reaction is allowed to proceed for a longer time.

The entire disclosure of Japanese Patent Application No. 9-305071 filed on Oct. 21, 1997 including specification, claims and summary are incorporated herein by reference in its entirety.

What is claimed is:

1. A nucleic acid encoding an maltopentaose-producing α-amylase, wherein the maltopentaose is a mutant of the amino acid sequence of the maltopentaose-producing (α-amylase produced by Pseudomonas sp. KO-8940 in which the trypotophan residue at the 57$^{th}$ position or the tyrosine at the 139$^{th}$ position in the amino acid sequence is substituted with an amino acid residue selected from the group consisting of phenylalanine, histidine and leucine.

2. The nucleic acid of claim 1, wherein the tryptophan residue at the 57$^{th}$ position in the amino acid sequence of the maltopentaose-producing α-amylase produced by Pseudomonas sp. KO-8940 is substituted with a phenylalanine residue.

3. The nucleic acid of claim 1, wherein the tryptophan residue at the 57$^{th}$ position in the amino acid sequence of the maltopentaose-producing α-amylase produced by Pseudomonas sp. KO-8940 is substituted with a histidine residue.

4. The nucleic acid of claim 1, wherein the tryptophan residue at the 57$^{th}$ position in the amino acid sequence of the maltopentaose-producing α-amylase produced by Pseudomonas sp. KO-8940 is substituted with a leucine residue.

5. The nucleic acid of claim 1, wherein the tryptophan residue at the 139$^{th}$ position in the amino acid sequence of the maltopentaose-producing α-amylase produced by Pseudomonas sp. KO-8940 is substituted with a phenylalanine residue.

6. The nucleic acid of claim 1, wherein the tryptophan residue at the 139$^{th}$ position in the amino acid sequence of the maltopentaose-producing α-amylase produced by Pseudomonas sp. KO-8940 is substituted with a histidine residue.

7. The nucleic acid of claim 1, wherein the tryptophan residue at the 139$^{th}$ position in the amino acid sequence of the maltopentaose-producing α-amylase produced by Pseudomonas sp. KO-8940 is substituted with a leucine residue.

8. The nucleic acid of claim 1, which is isolated and purified.

9. A plasmid comprising the nucleic acid of claim 1.

10. The plasmid of claim 9, which comprises SEQ ID NO: 3.

11. The plasmid of claim 9, which comprises SEQ ID NO: 4.

12. The plasmid of claim 9, which comprises SEQ ID NO: 5.

13. The plasmid of claim 9, which comprises SEQ ID NO: 6.

14. The plasmid of claim 9, which comprises SEQ ID NO: 7.

15. The plasmid of claim 9, which comprises SEQ ID NO: 8.

16. The plasmid of claim 9, wherein the maltopentaose-producing α-amylase has the amino acid sequence of SEQ ID NO: 9.

17. The plasmid of claim 9, wherein the maltopentaose-producing α-amylase has the amino acid sequence of SEQ ID NO: 10.

18. The plasmid of claim 9, wherein the maltopentaose-producing α-amylase has the amino acid sequence of SEQ ID NO: 11.

19. The plasmid of claim 9, wherein the maltopentaose-producing α-amylase has the amino acid sequence of SEQ ID NO: 12.

20. The plasmid of claim 9, wherein the maltopentaose-producing α-amylase has the amino acid sequence of SEQ ID NO: 13.

21. The plasmid of claim 9, wherein the maltopentaose-producing α-amylase has the amino acid sequence of SEQ ID NO: 14.

22. An *E. coli* transformed with the plasmid of claim 9.

23. The transformed *E. coli* of claim 22, which is *E. coli* FERM-BP 6116.

24. The transformed *E. coli* of claim 22, which is *E. coli* FERM-BP 6119.

25. The transformed *E. coli* of claim 22, which is *E. coli* FERM-BP 6115.

26. The transformed *E. coli* of claim 22, which is *E. coli* FERM-BP 6117.

27. The transformed *E. coli* of claim 22, which is *E. coli* FERM-BP 6118.

28. The transformed *E. coli* of claim 22, which is *E. coli* FERM-BP 6114.

29. A method of producing an maltopentaose-producing α-amylase, comprising culturing the transformed *E. coli* of claim 16 in a culture medium to produce the maltopentaose-producing α-amylase.

30. The method of claim 29, further comprising isolating the maltopentaose-producing α-amylase.

* * * * *

SEQUENCE LISTING

<160> NUMBER OF SEQ ID NOS: 14

<210> SEQ ID NO 1
<211> LENGTH: 23
<212> TYPE: DNA
<213> ORGANISM: Pseudomonas sp., Strain KO-8940
<220> FEATURE:
<221> NAME/KEY: mutation
<222> LOCATION: (1)..(23)
<223> OTHER INFORMATION: METHOD OF DETERMINING CHARACTERISTIC: S
<220> FEATURE:
<223> OTHER INFORMATION: SYNTHETIC MIXED OLIGONUCLEOTIDE

<400> SEQUENCE: 1
ggtagcgcat shrccacggg acg                                               23

<210> SEQ ID NO 2
<211> LENGTH: 25
<212> TYPE: DNA
<213> ORGANISM: Pseudomonas sp., Strain KO-8940
<220> FEATURE:
<223> OTHER INFORMATION: SYNTHETIC MIXED OLIGONUCLEOTIDE
<220> FEATURE:
<221> NAME/KEY: mutation
<222> LOCATION: (1)..(25)
<223> OTHER INFORMATION: METHOD OF DETERMINING CHARACTERISTIC: S

<400> SEQUENCE: 2
gttcgcgtca ccgwrgttgg tgatg                                             25

<210> SEQ ID NO 3
<211> LENGTH: 1981
<212> TYPE: DNA
<213> ORGANISM: Pseudomonas sp., Strain KO-8940
<220> FEATURE:
<221> NAME/KEY: CDS
<222> LOCATION: (7)..(1848)
<220> FEATURE:
<221> NAME/KEY: mat_peptide
<222> LOCATION: (85)..(1848)
<223> OTHER INFORMATION: METHOD OF DETERMINING CHARACTERISTIC: E
<220> FEATURE:
<223> OTHER INFORMATION: MUTATED GENOMIC DNA
<220> FEATURE:
<223> OTHER INFORMATION: PLASMID pOS3410F57

<400> SEQUENCE: 3

```
gaattc atg tcg cgc agg ctg gcg ctg gcc ctg gcc gcc agt gcc gtc            48
       Met Ser Arg Arg Leu Ala Leu Ala Leu Ala Ala Ser Ala Val
           -25              -20                 -15 ctg gcc ggg ccc tgg gcg gtc ggc gcg gtg cag gcg cag tcc gcg ccg           96
Leu Ala Gly Pro Trp Ala Val Gly Ala Val Gln Ala Gln Ser Ala Pro
     -10                 -5                 -1   1 cgc acg gcc ttc gtg cag ctt ttc gag tgg aag tgg acc gac gtc gcc          144
Arg Thr Ala Phe Val Gln Leu Phe Glu Trp Lys Trp Thr Asp Val Ala
 5                  10                  15                  20 cgg gag tgc gag acc tac ctc ggc ccc aag ggt ttc gcg gcc gtg cag          192
Arg Glu Cys Glu Thr Tyr Leu Gly Pro Lys Gly Phe Ala Ala Val Gln
             25                  30                  35 atc tcg ccg ccc aac gag cac aac tgg gtc agc agc ggc gac ggc gcg          240
Ile Ser Pro Pro Asn Glu His Asn Trp Val Ser Ser Gly Asp Gly Ala
         40                  45                  50 ccc tac ccg tgg ttc atg cgc tac cag ccg gtc agc tac agc ctg gac          288
Pro Tyr Pro Trp Phe Met Arg Tyr Gln Pro Val Ser Tyr Ser Leu Asp
     55                  60                  65
```

-continued

| | |
|---|---|
| cgc agc cgc agc ggc act cgc gcc gag ttc cag gac atg gtc aac cgc<br>Arg Ser Arg Ser Gly Thr Arg Ala Glu Phe Gln Asp Met Val Asn Arg<br>70            75                  80 | 336 |
| tgc aac gca gca ggc gtg ggc atc tac gtc gac gcg gtg atc aac cac<br>Cys Asn Ala Ala Gly Val Gly Ile Tyr Val Asp Ala Val Ile Asn His<br>85              90                  95                  100 | 384 |
| atg tcg ggt ggc aac ggc ggc acc tcg agc gca ggg cgc agc tgg agc<br>Met Ser Gly Gly Asn Gly Gly Thr Ser Ser Ala Gly Arg Ser Trp Ser<br>                   105                 110                 115 | 432 |
| cac cac aac tat ccg ggc ctg tac ggc tcg cag gac ttc cat cac ccg<br>His His Asn Tyr Pro Gly Leu Tyr Gly Ser Gln Asp Phe His His Pro<br>               120                 125                 130 | 480 |
| gtg tgc gcc atc acc aac tac ggt gac gcg aac aac gtg cag aac tgc<br>Val Cys Ala Ile Thr Asn Tyr Gly Asp Ala Asn Asn Val Gln Asn Cys<br>           135                 140                 145 | 528 |
| gag ctc tcg ggc ctg cag gac ctg aac acc ggc agc agc tac gtg cgc<br>Glu Leu Ser Gly Leu Gln Asp Leu Asn Thr Gly Ser Ser Tyr Val Arg<br>150                 155                 160 | 576 |
| ggc aag atc tcc gac tac ctg gtc gac ctg gtc cag atg ggc gtc aag<br>Gly Lys Ile Ser Asp Tyr Leu Val Asp Leu Val Gln Met Gly Val Lys<br>165                 170                 175                 180 | 624 |
| ggc ttg cgc gtc gat gcg gcc aag cac atc agc ccg acg gac ctg ggt<br>Gly Leu Arg Val Asp Ala Ala Lys His Ile Ser Pro Thr Asp Leu Gly<br>                   185                 190                 195 | 672 |
| gcc atc atc gac agc gtc aac gcg cgc acc ggt gcc gca cgg cca ttc<br>Ala Ile Ile Asp Ser Val Asn Ala Arg Thr Gly Ala Ala Arg Pro Phe<br>               200                 205                 210 | 720 |
| tgg ttc ctg gag gtg atc ggc gcg ccg ggc gag gcg gtg cag ccc agc<br>Trp Phe Leu Glu Val Ile Gly Ala Pro Gly Glu Ala Val Gln Pro Ser<br>           215                 220                 225 | 768 |
| cag tac ttc ggg ctc ggc ggc ggg cag gtc acg gtg acc gag ttc gcc<br>Gln Tyr Phe Gly Leu Gly Gly Gly Gln Val Thr Val Thr Glu Phe Ala<br>230                 235                 240 | 816 |
| tac ggc aag gag ctc tac ggc aag ttc gcc ggc ggc ggc aag ctg gcc<br>Tyr Gly Lys Glu Leu Tyr Gly Lys Phe Ala Gly Gly Gly Lys Leu Ala<br>245                 250                 255                 260 | 864 |
| gac ctg cag acc ttc ggc ccc agc tgg aac ctg atg ccc agc agc aag<br>Asp Leu Gln Thr Phe Gly Pro Ser Trp Asn Leu Met Pro Ser Ser Lys<br>                   265                 270                 275 | 912 |
| gcc atc gct ttc gtc gac aac cac gac aag cag cgc ggc cac ggc ggc<br>Ala Ile Ala Phe Val Asp Asn His Asp Lys Gln Arg Gly His Gly Gly<br>               280                 285                 290 | 960 |
| ggg ggc ggc tac gtc acc tat cac cac ggc agc acc tac gac ctg gcg<br>Gly Gly Gly Tyr Val Thr Tyr His His Gly Ser Thr Tyr Asp Leu Ala<br>           295                 300                 305 | 1008 |
| aac atc ttc atg ctg gcc tgg ccc tat ggc tac ccg gcg ctg atg tca<br>Asn Ile Phe Met Leu Ala Trp Pro Tyr Gly Tyr Pro Ala Leu Met Ser<br>310                 315                 320 | 1056 |
| gct acg gct tca acc agg gca gca gct acg aca cca gct acg gcc cgc<br>Ala Thr Ala Ser Thr Arg Ala Ala Ala Thr Thr Pro Ala Thr Ala Arg<br>325                 330                 335                 340 | 1104 |
| cgc act aca gcg acg gct cga ccc ggg ggc cgt ggg acc gga acc ccg<br>Arg Thr Thr Ala Thr Ala Arg Pro Gly Gly Arg Gly Thr Gly Thr Pro<br>                   345                 350                 355 | 1152 |
| cca gcc cgg gtg ctt caa cca gac cgt ggg tgg ctg ggt ctg cga gca<br>Pro Ala Arg Val Leu Gln Pro Asp Arg Gly Trp Leu Gly Leu Arg Ala<br>               360                 365                 370 | 1200 |
| ccg ctg gcg cgg cat cgg caa cat ggt ggc ctt ccg caa cgc cac cgt<br>Pro Leu Ala Arg His Arg Gln His Gly Gly Leu Pro Gln Arg His Arg<br>375                 380                 385 | 1248 |

-continued

```
gga caa ctg gtt cgt cag cga ctg gtg gag caa cgg caa caa cca gat    1296
Gly Gln Leu Val Arg Gln Arg Leu Val Glu Gln Arg Gln Gln Pro Asp
    390                 395                 400 cgc ctt cgg ccg cgg cga caa ggg ctt cgt cgt cat caa caa gga agg    1344
Arg Leu Arg Pro Arg Arg Gln Gly Leu Arg Arg His Gln Gln Gly Arg
405                 410                 415                 420 tac ggc gct gac gca gct tcc aga cca gcc tgc cgg ccg ggc gta ttg    1392
Tyr Gly Ala Asp Ala Ala Ser Arg Pro Ala Cys Arg Pro Gly Val Leu
                425                 430                 435 cga cgt gat ctc cgg cga ctt cgc caa cgg cag ctg cac cgg cac ggt    1440
Arg Arg Asp Leu Arg Arg Leu Arg Gln Arg Gln Leu His Arg His Gly
            440                 445                 450 ggt gac cgt gga tgc agg cgg cca cgc gat gct gtc cgc acc cgc tta    1488
Gly Asp Arg Gly Cys Arg Arg Pro Arg Asp Ala Val Arg Thr Arg Leu
        455                 460                 465 tgg cgc ggc ggc gat cca cgt cgg tgc gcg cat cgg cga cac gca gca    1536
Trp Arg Gly Gly Asp Pro Arg Arg Cys Ala His Arg Arg His Ala Ala
    470                 475                 480 ggt gca gca gtg ctc agc ttg acc ttc aac gag acg gcc gac acc gtg    1584
Gly Ala Ala Val Leu Ser Leu Thr Phe Asn Glu Thr Ala Asp Thr Val
485                 490                 495                 500 tgg ggc cag aac ctc ttc gtc gtc ggc aac gtc ggc gcg ctc ggc aac    1632
Trp Gly Gln Asn Leu Phe Val Val Gly Asn Val Gly Ala Leu Gly Asn
                505                 510                 515 tgg gcg ccc gcg gcc ggg gcg gcg atg acc tgg atc tcc ggc agc ggc    1680
Trp Ala Pro Ala Ala Gly Ala Ala Met Thr Trp Ile Ser Gly Ser Gly
            520                 525                 530 agc acc ggc cag tgg cgt gcg acg gtg cag ctg ccc gcc gac acg ccg    1728
Ser Thr Gly Gln Trp Arg Ala Thr Val Gln Leu Pro Ala Asp Thr Pro
        535                 540                 545 gtg cag tac aag tac gtg aag aag gac ggc gcc ggc aac gtg gtg tgg    1776
Val Gln Tyr Lys Tyr Val Lys Lys Asp Gly Ala Gly Asn Val Val Trp
    550                 555                 560 gaa agc ggc ggc aac cgc gtg gtg acg acg ccc gcg ccc ggg gcg acg    1824
Glu Ser Gly Gly Asn Arg Val Val Thr Thr Pro Ala Pro Gly Ala Thr
565                 570                 575                 580 atc gcc gtc aac gac agc tgg aag tgacggccgg gggcgccagg acgacaaggc   1878
Ile Ala Val Asn Asp Ser Trp Lys
                585 cctgagcgcc tcgtacaccg tgcccagcgt ggtggtagtc caactggccc gactggctct   1938 tctggttgct gagcttgcgg ttgtcgcgcg tcactgtggt acc                     1981

<210> SEQ ID NO 4
<211> LENGTH: 1981
<212> TYPE: DNA
<213> ORGANISM: Pseudomonas sp., Strain KO-8940
<220> FEATURE:
<221> NAME/KEY: CDS
<222> LOCATION: (7)..(1848)
<220> FEATURE:
<221> NAME/KEY: mat_peptide
<222> LOCATION: (85)..(1848)
<223> OTHER INFORMATION: METHOD OF DETERMINING CHARACTERISTIC: E
<220> FEATURE:
<223> OTHER INFORMATION: MUTATED GENOMIC DNA
<220> FEATURE:
<223> OTHER INFORMATION: PLASMID pOS3410H57

<400> SEQUENCE: 4 gaattc atg tcg cgc agg ctg gcg ctg gcc ctg gcc gcc agt gcc gtc      48
       Met Ser Arg Arg Leu Ala Leu Ala Leu Ala Ala Ser Ala Val
           -25                 -20                 -15
```

-continued

| | | |
|---|---|---|
| ctg gcc ggg ccc tgg gcg gtc ggc gcg gtg cag gcg cag tcc gcg ccg<br>Leu Ala Gly Pro Trp Ala Val Gly Ala Val Gln Ala Gln Ser Ala Pro<br>         -10               -5                   -1   1 | 96 |
| cgc acg gcc ttc gtg cag ctt ttc gag tgg aag tgg acc gac gtc gcc<br>Arg Thr Ala Phe Val Gln Leu Phe Glu Trp Lys Trp Thr Asp Val Ala<br>5                   10                 15                 20 | 144 |
| cgg gag tgc gag acc tac ctc ggc ccc aag ggt ttc gcg gcc gtg cag<br>Arg Glu Cys Glu Thr Tyr Leu Gly Pro Lys Gly Phe Ala Ala Val Gln<br>               25                 30                 35 | 192 |
| atc tcg ccg ccc aac gag cac aac tgg gtc agc agc ggc gac ggc gcg<br>Ile Ser Pro Pro Asn Glu His Asn Trp Val Ser Ser Gly Asp Gly Ala<br>         40                   45                 50 | 240 |
| ccc tac ccg tgg cac atg cgc tac cag ccg gtc agc tac agc ctg gac<br>Pro Tyr Pro Trp His Met Arg Tyr Gln Pro Val Ser Tyr Ser Leu Asp<br>              55                 60                 65 | 288 |
| cgc agc cgc agc ggc act cgc gcc gag ttc cag gac atg gtc aac cgc<br>Arg Ser Arg Ser Gly Thr Arg Ala Glu Phe Gln Asp Met Val Asn Arg<br>   70                   75                 80 | 336 |
| tgc aac gca gca ggc gtg ggc atc tac gtc gac gcg gtg atc aac cac<br>Cys Asn Ala Ala Gly Val Gly Ile Tyr Val Asp Ala Val Ile Asn His<br>85                  90                 95               100 | 384 |
| atg tcg ggt ggc aac ggc ggc acc tcg agc gca ggg cgc agc tgg agc<br>Met Ser Gly Gly Asn Gly Gly Thr Ser Ser Ala Gly Arg Ser Trp Ser<br>              105                110              115 | 432 |
| cac cac aac tat ccg ggc ctg tac ggc tcg cag gac ttc cat cac ccg<br>His His Asn Tyr Pro Gly Leu Tyr Gly Ser Gln Asp Phe His His Pro<br>         120                  125               130 | 480 |
| gtg tgc gcc atc acc aac tac ggt gac gcg aac aac gtg cag aac tgc<br>Val Cys Ala Ile Thr Asn Tyr Gly Asp Ala Asn Asn Val Gln Asn Cys<br>              135                140              145 | 528 |
| gag ctc tcg ggc ctg cag gac ctg aac acc ggc agc agc tac gtg cgc<br>Glu Leu Ser Gly Leu Gln Asp Leu Asn Thr Gly Ser Ser Tyr Val Arg<br>         150                  155               160 | 576 |
| ggc aag atc tcc gac tac ctg gtc gac ctg gtc cag atg ggc gtc aag<br>Gly Lys Ile Ser Asp Tyr Leu Val Asp Leu Val Gln Met Gly Val Lys<br>165                 170                175              180 | 624 |
| ggc ttg cgc gtc gat gcg gcc aag cac atc agc ccg acg gac ctg ggt<br>Gly Leu Arg Val Asp Ala Ala Lys His Ile Ser Pro Thr Asp Leu Gly<br>              185                190              195 | 672 |
| gcc atc atc gac agc gtc aac gcg cgc acc ggt gcc gca cgg cca ttc<br>Ala Ile Ile Asp Ser Val Asn Ala Arg Thr Gly Ala Ala Arg Pro Phe<br>         200                  205               210 | 720 |
| tgg ttc ctg gag gtg atc ggc gcg ccg ggc gag gcg gtg cag ccc agc<br>Trp Phe Leu Glu Val Ile Gly Ala Pro Gly Glu Ala Val Gln Pro Ser<br>              215                220              225 | 768 |
| cag tac ttc ggg ctc ggc ggc ggg cag gtc acg gtg acc gag ttc gcc<br>Gln Tyr Phe Gly Leu Gly Gly Gly Gln Val Thr Val Thr Glu Phe Ala<br>         230                  235               240 | 816 |
| tac ggc aag gag ctc tac ggc aag ttc gcc ggc ggc ggc aag ctg gcc<br>Tyr Gly Lys Glu Leu Tyr Gly Lys Phe Ala Gly Gly Gly Lys Leu Ala<br>245                 250                255              260 | 864 |
| gac ctg cag acc ttc ggc ccc agc tgg aac ctg atg ccc agc agc aag<br>Asp Leu Gln Thr Phe Gly Pro Ser Trp Asn Leu Met Pro Ser Ser Lys<br>              265                270              275 | 912 |
| gcc atc gct ttc gtc gac aac cac gac aag cag cgc ggc cac ggc ggc<br>Ala Ile Ala Phe Val Asp Asn His Asp Lys Gln Arg Gly His Gly Gly<br>         280                  285               290 | 960 |
| ggg ggc ggc tac gtc acc tat cac cac ggc agc acc tac gac ctg gcg<br>Gly Gly Gly Tyr Val Thr Tyr His His Gly Ser Thr Tyr Asp Leu Ala | 1008 |

-continued

```
            295                 300                 305
aac atc ttc atg ctg gcc tgg ccc tat ggc tac ccg gcg ctg atg tca       1056
Asn Ile Phe Met Leu Ala Trp Pro Tyr Gly Tyr Pro Ala Leu Met Ser
    310                 315                 320 gct acg gct tca acc agg gca gca gct acg aca cca gct acg gcc cgc       1104
Ala Thr Ala Ser Thr Arg Ala Ala Ala Thr Thr Pro Ala Thr Ala Arg
325                 330                 335                 340 cgc act aca gcg acg gct cga ccc ggg ggc cgt ggg acc gga acc ccg       1152
Arg Thr Thr Ala Thr Ala Arg Pro Gly Gly Arg Gly Thr Gly Thr Pro
                345                 350                 355 cca gcc cgg gtg ctt caa cca gac cgt ggg tgg ctg ggt ctg cga gca       1200
Pro Ala Arg Val Leu Gln Pro Asp Arg Gly Trp Leu Gly Leu Arg Ala
            360                 365                 370 ccg ctg gcg cgg cat cgg caa cat ggt ggc ctt ccg caa cgc cac cgt       1248
Pro Leu Ala Arg His Arg Gln His Gly Gly Leu Pro Gln Arg His Arg
        375                 380                 385 gga caa ctg gtt cgt cag cga ctg gtg gag caa cgg caa caa cca gat       1296
Gly Gln Leu Val Arg Gln Arg Leu Val Glu Gln Arg Gln Gln Pro Asp
    390                 395                 400 cgc ctt cgg ccg cgg cga caa ggg ctt cgt cgt cat caa caa gga agg       1344
Arg Leu Arg Pro Arg Arg Gln Gly Leu Arg Arg His Gln Gln Gly Arg
405                 410                 415                 420 tac ggc gct gac gca gct tcc aga cca gcc tgc cgg ccg ggc gta ttg       1392
Tyr Gly Ala Asp Ala Ala Ser Arg Pro Ala Cys Arg Pro Gly Val Leu
                425                 430                 435 cga cgt gat ctc cgg cga ctt cgc caa cgg cag ctg cac cgg cac ggt       1440
Arg Arg Asp Leu Arg Arg Leu Arg Gln Arg Gln Leu His Arg His Gly
            440                 445                 450 ggt gac cgt gga tgc agg cgg cca cgc gat gct gtc cgc acc cgc tta       1488
Gly Asp Arg Gly Cys Arg Arg Pro Arg Asp Ala Val Arg Thr Arg Leu
        455                 460                 465 tgg cgc ggc ggc gat cca cgt cgg tgc gcg cat cgg cga cac gca gca       1536
Trp Arg Gly Gly Asp Pro Arg Arg Cys Ala His Arg Arg His Ala Ala
    470                 475                 480 ggt gca gca gtg ctc agc ttg acc ttc aac gag acg gcc gac acc gtg       1584
Gly Ala Ala Val Leu Ser Leu Thr Phe Asn Glu Thr Ala Asp Thr Val
485                 490                 495                 500 tgg ggc cag aac ctc ttc gtc gtc ggc aac gtc ggc gcg ctc ggc aac       1632
Trp Gly Gln Asn Leu Phe Val Val Gly Asn Val Gly Ala Leu Gly Asn
                505                 510                 515 tgg gcg ccc gcg gcc ggg gcg gcg atg acc tgg atc tcc ggc agc ggc       1680
Trp Ala Pro Ala Ala Gly Ala Ala Met Thr Trp Ile Ser Gly Ser Gly
            520                 525                 530 agc acc ggc cag tgg cgt gcg acg gtg cag ctg ccc gcc gac acg ccg       1728
Ser Thr Gly Gln Trp Arg Ala Thr Val Gln Leu Pro Ala Asp Thr Pro
        535                 540                 545 gtg cag tac aag tac gtg aag aag gac ggc gcc ggc aac gtg gtg tgg       1776
Val Gln Tyr Lys Tyr Val Lys Lys Asp Gly Ala Gly Asn Val Val Trp
    550                 555                 560 gaa agc ggc ggc aac cgc gtg gtg acg acg ccc gcg ccc ggg gcg acg       1824
Glu Ser Gly Gly Asn Arg Val Val Thr Thr Pro Ala Pro Gly Ala Thr
565                 570                 575                 580 atc gcc gtc aac gac agc tgg aag tgacggccgg gggcgccagg acgacaaggc     1878
Ile Ala Val Asn Asp Ser Trp Lys
                585 cctgagcgcc tcgtacaccg tgcccagcgt ggtggtagtc caactggccc gactggctct    1938 tctggttgct gagcttgcgg ttgtcgcgcg tcactgtggt acc                      1981
```

```
<210> SEQ ID NO 5
<211> LENGTH: 1981
<212> TYPE: DNA
<213> ORGANISM: Pseudomonas sp., Strain KO-8940
<220> FEATURE:
<221> NAME/KEY: CDS
<222> LOCATION: (7)..(1848)
<220> FEATURE:
<221> NAME/KEY: mat_peptide
<222> LOCATION: (85)..(1848)
<223> OTHER INFORMATION: METHOD OF DETERMINING CHARACTERISTIC: E
<220> FEATURE:
<223> OTHER INFORMATION: MUTATED GENOMIC DNA
<220> FEATURE:
<223> OTHER INFORMATION: PLASMID pOS3410OL57

<400> SEQUENCE: 5 gaattc atg tcg cgc agg ctg gcg ctg gcc ctg gcc gcc agt gcc gtc        48
       Met Ser Arg Arg Leu Ala Leu Ala Leu Ala Ala Ser Ala Val
           -25             -20             -15 ctg gcc ggg ccc tgg gcg gtc ggc gcg gtg cag gcg cag tcc gcg ccg       96
Leu Ala Gly Pro Trp Ala Val Gly Ala Val Gln Ala Gln Ser Ala Pro
        -10              -5              -1   1 cgc acg gcc ttc gtg cag ctt ttc gag tgg aag tgg acc gac gtc gcc      144
Arg Thr Ala Phe Val Gln Leu Phe Glu Trp Lys Trp Thr Asp Val Ala
 5              10              15              20 cgg gag tgc gag acc tac ctc ggc ccc aag ggt ttc gcg gcc gtg cag      192
Arg Glu Cys Glu Thr Tyr Leu Gly Pro Lys Gly Phe Ala Ala Val Gln
                25              30              35 atc tcg ccg ccc aac gag cac aac tgg gtc agc agc ggc gac ggc gcg      240
Ile Ser Pro Pro Asn Glu His Asn Trp Val Ser Ser Gly Asp Gly Ala
            40              45              50 ccc tac ccg tgg ctc atg cgc tac cag ccg gtc agc tac agc ctg gac      288
Pro Tyr Pro Trp Leu Met Arg Tyr Gln Pro Val Ser Tyr Ser Leu Asp
        55              60              65 cgc agc cgc agc ggc act cgc gcc gag ttc cag gac atg gtc aac cgc      336
Arg Ser Arg Ser Gly Thr Arg Ala Glu Phe Gln Asp Met Val Asn Arg
     70              75              80 tgc aac gca gca ggc gtg ggc atc tac gtc gac gcg gtg atc aac cac      384
Cys Asn Ala Ala Gly Val Gly Ile Tyr Val Asp Ala Val Ile Asn His
 85              90              95              100 atg tcg ggt ggc aac ggc ggc acc tcg agc gca ggg cgc agc tgg agc      432
Met Ser Gly Gly Asn Gly Gly Thr Ser Ser Ala Gly Arg Ser Trp Ser
                105             110             115 cac cac aac tat ccg ggc ctg tac ggc tcg cag gac ttc cat cac ccg      480
His His Asn Tyr Pro Gly Leu Tyr Gly Ser Gln Asp Phe His His Pro
            120             125             130 gtg tgc gcc atc acc aac tac ggt gac gcg aac aac gtg cag aac tgc      528
Val Cys Ala Ile Thr Asn Tyr Gly Asp Ala Asn Asn Val Gln Asn Cys
        135             140             145 gag ctc tcg ggc ctg cag gac ctg aac acc ggc agc agc tac gtg cgc      576
Glu Leu Ser Gly Leu Gln Asp Leu Asn Thr Gly Ser Ser Tyr Val Arg
    150             155             160 ggc aag atc tcc gac tac ctg gtc gac ctg gtc cag atg ggc gtc aag      624
Gly Lys Ile Ser Asp Tyr Leu Val Asp Leu Val Gln Met Gly Val Lys
165             170             175             180 ggc ttg cgc gtc gat gcg gcc aag cac atc agc ccg acg gac ctg ggt      672
Gly Leu Arg Val Asp Ala Ala Lys His Ile Ser Pro Thr Asp Leu Gly
                185             190             195 gcc atc atc gac agc gtc aac gcg cgc acc ggt gcc gca cgg cca ttc      720
Ala Ile Ile Asp Ser Val Asn Ala Arg Thr Gly Ala Ala Arg Pro Phe
            200             205             210 tgg ttc ctg gag gtg atc ggc gcg ccg ggc gag gcg gtg cag ccc agc      768
```

```
                Trp Phe Leu Glu Val Ile Gly Ala Pro Gly Glu Ala Val Gln Pro Ser
                    215                 220                 225 cag tac ttc ggg ctc ggc ggc ggg cag gtc acg gtg acc gag ttc gcc          816
Gln Tyr Phe Gly Leu Gly Gly Gly Gln Val Thr Val Thr Glu Phe Ala
    230                 235                 240 tac ggc aag gag ctc tac ggc aag ttc gcc ggc ggc aag ctg gcc              864
Tyr Gly Lys Glu Leu Tyr Gly Lys Phe Ala Gly Gly Gly Lys Leu Ala
245                 250                 255                 260 gac ctg cag acc ttc ggc ccc agc tgg aac ctg atg ccc agc agc aag          912
Asp Leu Gln Thr Phe Gly Pro Ser Trp Asn Leu Met Pro Ser Ser Lys
                265                 270                 275 gcc atc gct ttc gtc gac aac cac gac aag cag cgc ggc cac ggc ggc          960
Ala Ile Ala Phe Val Asp Asn His Asp Lys Gln Arg Gly His Gly Gly
            280                 285                 290 ggg ggc ggc tac gtc acc tat cac cac ggc agc acc tac gac ctg gcg         1008
Gly Gly Gly Tyr Val Thr Tyr His His Gly Ser Thr Tyr Asp Leu Ala
        295                 300                 305 aac atc ttc atg ctg gcc tgg ccc tat ggc tac ccg gcg ctg atg tca         1056
Asn Ile Phe Met Leu Ala Trp Pro Tyr Gly Tyr Pro Ala Leu Met Ser
    310                 315                 320 gct acg gct tca acc agg gca gca gct acg aca cca gct acg gcc cgc         1104
Ala Thr Ala Ser Thr Arg Ala Ala Ala Thr Thr Pro Ala Thr Ala Arg
325                 330                 335                 340 cgc act aca gcg acg gct cga ccc ggg ggc cgt ggg acc gga acc ccg         1152
Arg Thr Thr Ala Thr Ala Arg Pro Gly Gly Arg Gly Thr Gly Thr Pro
                345                 350                 355 cca gcc cgg gtg ctt caa cca gac cgt ggg tgg ctg ggt ctg cga gca         1200
Pro Ala Arg Val Leu Gln Pro Asp Arg Gly Trp Leu Gly Leu Arg Ala
            360                 365                 370 ccg ctg gcg cgg cat cgg caa cat ggt ggc ctt ccg caa cgc cac cgt         1248
Pro Leu Ala Arg His Arg Gln His Gly Gly Leu Pro Gln Arg His Arg
        375                 380                 385 gga caa ctg gtt cgt cag cga ctg gtg gag caa cgg caa caa cca gat         1296
Gly Gln Leu Val Arg Gln Arg Leu Val Glu Gln Arg Gln Gln Pro Asp
    390                 395                 400 cgc ctt cgg ccg cgg cga caa ggg ctt cgt cgt cat caa caa gga agg         1344
Arg Leu Arg Pro Arg Arg Gln Gly Leu Arg Arg His Gln Gln Gly Arg
405                 410                 415                 420 tac ggc gct gac gca gct tcc aga cca gcc tgc cgg ccg ggc gta ttg         1392
Tyr Gly Ala Asp Ala Ala Ser Arg Pro Ala Cys Arg Pro Gly Val Leu
                425                 430                 435 cga cgt gat ctc cgg cga ctt cgc caa cgg cag ctg cac cgg cac ggt         1440
Arg Arg Asp Leu Arg Arg Leu Arg Gln Arg Gln Leu His Arg His Gly
            440                 445                 450 ggt gac cgt gga tgc agg cgg cca cgc gat gct gtc cgc acc cgc tta         1488
Gly Asp Arg Gly Cys Arg Arg Pro Arg Asp Ala Val Arg Thr Arg Leu
        455                 460                 465 tgg cgc ggc ggc gat cca cgt cgg tgc gcg cat cgg cga cac gca gca         1536
Trp Arg Gly Gly Asp Pro Arg Arg Cys Ala His Arg Arg His Ala Ala
    470                 475                 480 ggt gca gca gtg ctc agc ttg acc ttc aac gag acg gcc gac acc gtg         1584
Gly Ala Ala Val Leu Ser Leu Thr Phe Asn Glu Thr Ala Asp Thr Val
485                 490                 495                 500 tgg ggc cag aac ctc ttc gtc gtc ggc aac gtc ggc gcg ctc ggc aac         1632
Trp Gly Gln Asn Leu Phe Val Val Gly Asn Val Gly Ala Leu Gly Asn
                505                 510                 515 tgg gcg ccc gcg gcc ggg gcg gcg atg acc tgg atc tcc ggc agc ggc         1680
Trp Ala Pro Ala Ala Gly Ala Ala Met Thr Trp Ile Ser Gly Ser Gly
            520                 525                 530
```

-continued

```
agc acc ggc cag tgg cgt gcg acg gtg cag ctg ccc gcc gac acg ccg      1728
Ser Thr Gly Gln Trp Arg Ala Thr Val Gln Leu Pro Ala Asp Thr Pro
        535                 540                 545 gtg cag tac aag tac gtg aag aag gac ggc gcc ggc aac gtg gtg tgg      1776
Val Gln Tyr Lys Tyr Val Lys Lys Asp Gly Ala Gly Asn Val Val Trp
550                 555                 560 gaa agc ggc ggc aac cgc gtg gtg acg acg ccc gcg ccc ggg gcg acg      1824
Glu Ser Gly Gly Asn Arg Val Val Thr Thr Pro Ala Pro Gly Ala Thr
565                 570                 575                 580 atc gcc gtc aac gac agc tgg aag tgacggccgg gggcgccagg acgacaaggc     1878
Ile Ala Val Asn Asp Ser Trp Lys
                585 cctgagcgcc tcgtacaccg tgcccagcgt ggtggtagtc caactggccc gactggctct    1938 tctggttgct gagcttgcgg ttgtcgcgcg tcactgtggt acc                      1981

<210> SEQ ID NO 6
<211> LENGTH: 1981
<212> TYPE: DNA
<213> ORGANISM: Pseudomonas sp., Strain KO-8940
<220> FEATURE:
<221> NAME/KEY: CDS
<222> LOCATION: (7)..(1848)
<220> FEATURE:
<221> NAME/KEY: mat_peptide
<222> LOCATION: (85)..(1848)
<220> FEATURE:
<223> OTHER INFORMATION: MUTATED GENOMIC DNA
<220> FEATURE:
<223> OTHER INFORMATION: PLASMID: pOS3410F139

<400> SEQUENCE: 6 gaattc atg tcg cgc agg ctg gcg ctg gcc ctg gcc gcc agt gcc gtc       48
       Met Ser Arg Arg Leu Ala Leu Ala Leu Ala Ala Ser Ala Val
           -25                 -20                 -15 ctg gcc ggg ccc tgg gcg gtc ggc gcg gtg cag gcg cag tcc gcg ccg      96
Leu Ala Gly Pro Trp Ala Val Gly Ala Val Gln Ala Gln Ser Ala Pro
        -10                  -5                  -1   1 cgc acg gcc ttc gtg cag ctt ttc gag tgg aag tgg acc gac gtc gcc      144
Arg Thr Ala Phe Val Gln Leu Phe Glu Trp Lys Trp Thr Asp Val Ala
 5                  10                  15                  20 cgg gag tgc gag acc tac ctc ggc ccc aag ggt ttc gcg gcc gtg cag      192
Arg Glu Cys Glu Thr Tyr Leu Gly Pro Lys Gly Phe Ala Ala Val Gln
                25                  30                  35 atc tcg ccg ccc aac gag cac aac tgg gtc agc agc ggc gac ggc gcg      240
Ile Ser Pro Pro Asn Glu His Asn Trp Val Ser Ser Gly Asp Gly Ala
            40                  45                  50 ccc tac ccg tgg tgg atg cgc tac cag ccg gtc agc tac agc ctg gac      288
Pro Tyr Pro Trp Trp Met Arg Tyr Gln Pro Val Ser Tyr Ser Leu Asp
        55                  60                  65 cgc agc cgc agc ggc act cgc gcc gag ttc cag gac atg gtc aac cgc      336
Arg Ser Arg Ser Gly Thr Arg Ala Glu Phe Gln Asp Met Val Asn Arg
 70                  75                  80 tgc aac gca gca ggc gtg ggc atc tac gtc gac gcg gtg atc aac cac      384
Cys Asn Ala Ala Gly Val Gly Ile Tyr Val Asp Ala Val Ile Asn His
85                  90                  95                  100 atg tcg ggt ggc aac ggc ggc acc tcg agc gca ggg cgc agc tgg agc      432
Met Ser Gly Gly Asn Gly Gly Thr Ser Ser Ala Gly Arg Ser Trp Ser
                105                 110                 115 cac cac aac tat ccg ggc ctg tac ggc tcg cag gac ttc cat cac ccg      480
His His Asn Tyr Pro Gly Leu Tyr Gly Ser Gln Asp Phe His His Pro
            120                 125                 130 gtg tgc gcc atc acc aac ttc ggt gac gcg aac aac gtg cag aac tgc      528
```

```
                Val Cys Ala Ile Thr Asn Phe Gly Asp Ala Asn Asn Val Gln Asn Cys
                            135                 140                 145 gag ctc tcg ggc ctg cag gac ctg aac acc ggc agc agc tac gtg cgc             576
Glu Leu Ser Gly Leu Gln Asp Leu Asn Thr Gly Ser Ser Tyr Val Arg
    150                 155                 160 ggc aag atc tcc gac tac ctg gtc gac ctg gtc cag atg ggc gtc aag             624
Gly Lys Ile Ser Asp Tyr Leu Val Asp Leu Val Gln Met Gly Val Lys
165                 170                 175                 180 ggc ttg cgc gtc gat gcg gcc aag cac atc agc ccg acg gac ctg ggt             672
Gly Leu Arg Val Asp Ala Ala Lys His Ile Ser Pro Thr Asp Leu Gly
                185                 190                 195 gcc atc atc gac agc gtc aac gcg cgc acc ggt gcc gca cgg cca ttc             720
Ala Ile Ile Asp Ser Val Asn Ala Arg Thr Gly Ala Ala Arg Pro Phe
            200                 205                 210 tgg ttc ctg gag gtg atc ggc gcg ccg ggc gag gcg gtg cag ccc agc             768
Trp Phe Leu Glu Val Ile Gly Ala Pro Gly Glu Ala Val Gln Pro Ser
        215                 220                 225 cag tac ttc ggg ctc ggc ggc ggg cag gtc acg gtg acc gag ttc gcc             816
Gln Tyr Phe Gly Leu Gly Gly Gly Gln Val Thr Val Thr Glu Phe Ala
    230                 235                 240 tac ggc aag gag ctc tac ggc aag ttc gcc ggc ggc ggc aag ctg gcc             864
Tyr Gly Lys Glu Leu Tyr Gly Lys Phe Ala Gly Gly Gly Lys Leu Ala
245                 250                 255                 260 gac ctg cag acc ttc ggc ccc agc tgg aac ctg atg ccc agc agc aag             912
Asp Leu Gln Thr Phe Gly Pro Ser Trp Asn Leu Met Pro Ser Ser Lys
                265                 270                 275 gcc atc gct ttc gtc gac aac cac gac aag cag cgc ggc cac ggc ggc             960
Ala Ile Ala Phe Val Asp Asn His Asp Lys Gln Arg Gly His Gly Gly
            280                 285                 290 ggg ggc ggc tac gtc acc tat cac cac ggc agc acc tac gac ctg gcg            1008
Gly Gly Gly Tyr Val Thr Tyr His His Gly Ser Thr Tyr Asp Leu Ala
        295                 300                 305 aac atc ttc atg ctg gcc tgg ccc tat ggc tac ccg gcg ctg atg tca            1056
Asn Ile Phe Met Leu Ala Trp Pro Tyr Gly Tyr Pro Ala Leu Met Ser
    310                 315                 320 gct acg gct tca acc agg gca gca gct acg aca cca gct acg gcc cgc            1104
Ala Thr Ala Ser Thr Arg Ala Ala Ala Thr Thr Pro Ala Thr Ala Arg
325                 330                 335                 340 cgc act aca gcg acg gct cga ccc ggg ggc cgt ggg acc gga acc ccg            1152
Arg Thr Thr Ala Thr Ala Arg Pro Gly Gly Arg Gly Thr Gly Thr Pro
                345                 350                 355 cca gcc cgg gtg ctt caa cca gac cgt ggg tgg ctg ggt ctg cga gca            1200
Pro Ala Arg Val Leu Gln Pro Asp Arg Gly Trp Leu Gly Leu Arg Ala
            360                 365                 370 ccg ctg gcg cgg cat cgg caa cat ggt ggc ctt ccg caa cgc cac cgt            1248
Pro Leu Ala Arg His Arg Gln His Gly Gly Leu Pro Gln Arg His Arg
        375                 380                 385 gga caa ctg gtt cgt cag cga ctg gtg gag caa cgg caa caa cca gat            1296
Gly Gln Leu Val Arg Gln Arg Leu Val Glu Gln Arg Gln Gln Pro Asp
    390                 395                 400 cgc ctt cgg ccg cgg cga caa ggg ctt cgt cgt cat caa caa gga agg            1344
Arg Leu Arg Pro Arg Arg Gln Gly Leu Arg Arg His Gln Gln Gly Arg
405                 410                 415                 420 tac ggc gct gac gca gct tcc aga cca gcc tgc cgg ccg ggc gta ttg            1392
Tyr Gly Ala Asp Ala Ala Ser Arg Pro Ala Cys Arg Pro Gly Val Leu
                425                 430                 435 cga cgt gat ctc cgg cga ctt cgc caa cgg cag ctg cac cgg cac ggt            1440
Arg Arg Asp Leu Arg Arg Leu Arg Gln Arg Gln Leu His Arg His Gly
            440                 445                 450
```

-continued

```
ggt gac cgt gga tgc agg cgg cca cgc gat gct gtc cgc acc cgc tta      1488
Gly Asp Arg Gly Cys Arg Arg Pro Arg Asp Ala Val Arg Thr Arg Leu
        455                 460                 465 tgg cgc ggc ggc gat cca cgt cgg tgc gcg cat cgg cga cac gca gca      1536
Trp Arg Gly Gly Asp Pro Arg Arg Cys Ala His Arg Arg His Ala Ala
    470                 475                 480 ggt gca gca gtg ctc agc ttg acc ttc aac gag acg gcc gac acc gtg      1584
Gly Ala Ala Val Leu Ser Leu Thr Phe Asn Glu Thr Ala Asp Thr Val
485                 490                 495                 500 tgg ggc cag aac ctc ttc gtc gtc ggc aac gtc ggc gcg ctc ggc aac      1632
Trp Gly Gln Asn Leu Phe Val Val Gly Asn Val Gly Ala Leu Gly Asn
                505                 510                 515 tgg gcg ccc gcg gcc ggg gcg gcg atg acc tgg atc tcc ggc agc ggc      1680
Trp Ala Pro Ala Ala Gly Ala Ala Met Thr Trp Ile Ser Gly Ser Gly
            520                 525                 530 agc acc ggc cag tgg cgt gcg acg gtg cag ctg ccc gcc gac acg ccg      1728
Ser Thr Gly Gln Trp Arg Ala Thr Val Gln Leu Pro Ala Asp Thr Pro
        535                 540                 545 gtg cag tac aag tac gtg aag aag gac ggc gcc ggc aac gtg gtg tgg      1776
Val Gln Tyr Lys Tyr Val Lys Lys Asp Gly Ala Gly Asn Val Val Trp
    550                 555                 560 gaa agc ggc ggc aac cgc gtg gtg acg acg ccc gcg ccc ggg gcg acg      1824
Glu Ser Gly Gly Asn Arg Val Val Thr Thr Pro Ala Pro Gly Ala Thr
565                 570                 575                 580 atc gcc gtc aac gac agc tgg aag tgacggccgg gggcgccagg acgacaaggc    1878
Ile Ala Val Asn Asp Ser Trp Lys
                585 cctgagcgcc tcgtacaccg tgcccagcgt ggtggtagtc caactggccc gactggctct   1938 tctggttgct gagcttgcgg ttgtcgcgcg tcactgtggt acc                     1981

<210> SEQ ID NO 7
<211> LENGTH: 1981
<212> TYPE: DNA
<213> ORGANISM: Pseudomonas sp., Strain KO-8940
<220> FEATURE:
<221> NAME/KEY: CDS
<222> LOCATION: (7)..(1848)
<220> FEATURE:
<221> NAME/KEY: mat_peptide
<222> LOCATION: (85)..(1848)
<223> OTHER INFORMATION: METHOD OF DETERMINING CHARACTERISTIC: E
<220> FEATURE:
<223> OTHER INFORMATION: MUTATED GENOMIC DNA
<220> FEATURE:
<223> OTHER INFORMATION: PLASMID: pOS3410H139

<400> SEQUENCE: 7 gaattc atg tcg cgc agg ctg gcg ctg gcc ctg gcc gcc agt gcc gtc        48
       Met Ser Arg Arg Leu Ala Leu Ala Leu Ala Ala Ser Ala Val
           -25                 -20                 -15 ctg gcc ggg ccc tgg gcg gtc ggc gcg gtg cag gcg cag tcc gcg ccg       96
Leu Ala Gly Pro Trp Ala Val Gly Ala Val Gln Ala Gln Ser Ala Pro
    -10                 -5                  -1   1 cgc acg gcc ttc gtg cag ctt ttc gag tgg aag tgg acc gac gtc gcc      144
Arg Thr Ala Phe Val Gln Leu Phe Glu Trp Lys Trp Thr Asp Val Ala
 5                  10                  15                  20 cgg gag tgc gag acc tac ctc ggc ccc aag ggt ttc gcg gcc gtg cag      192
Arg Glu Cys Glu Thr Tyr Leu Gly Pro Lys Gly Phe Ala Ala Val Gln
                25                  30                  35 atc tcg ccg ccc aac gag cac aac tgg gtc agc agc ggc gac ggc gcg      240
Ile Ser Pro Pro Asn Glu His Asn Trp Val Ser Ser Gly Asp Gly Ala
            40                  45                  50
```

```
ccc tac ccg tgg tgg atg cgc tac cag ccg gtc agc tac agc ctg gac       288
Pro Tyr Pro Trp Trp Met Arg Tyr Gln Pro Val Ser Tyr Ser Leu Asp
         55                  60                  65 cgc agc cgc agc ggc act cgc gcc gag ttc cag gac atg gtc aac cgc       336
Arg Ser Arg Ser Gly Thr Arg Ala Glu Phe Gln Asp Met Val Asn Arg
 70                  75                  80 tgc aac gca gca ggc gtg ggc atc tac gtc gac gcg gtg atc aac cac       384
Cys Asn Ala Ala Gly Val Gly Ile Tyr Val Asp Ala Val Ile Asn His
 85                  90                  95                 100 atg tcg ggt ggc aac ggc ggc acc tcg agc gca ggg cgc agc tgg agc       432
Met Ser Gly Gly Asn Gly Gly Thr Ser Ser Ala Gly Arg Ser Trp Ser
                105                 110                 115 cac cac aac tat ccg ggc ctg tac ggc tcg cag gac ttc cat cac ccg       480
His His Asn Tyr Pro Gly Leu Tyr Gly Ser Gln Asp Phe His His Pro
                120                 125                 130 gtg tgc gcc atc acc aac cac ggt gac gcg aac aac gtg cag aac tgc       528
Val Cys Ala Ile Thr Asn His Gly Asp Ala Asn Asn Val Gln Asn Cys
        135                 140                 145 gag ctc tcg ggc ctg cag gac ctg aac acc ggc agc agc tac gtg cgc       576
Glu Leu Ser Gly Leu Gln Asp Leu Asn Thr Gly Ser Ser Tyr Val Arg
150                 155                 160 ggc aag atc tcc gac tac ctg gtc gac ctg gtc cag atg ggc gtc aag       624
Gly Lys Ile Ser Asp Tyr Leu Val Asp Leu Val Gln Met Gly Val Lys
165                 170                 175                 180 ggc ttg cgc gtc gat gcg gcc aag cac atc agc ccg acg gac ctg ggt       672
Gly Leu Arg Val Asp Ala Ala Lys His Ile Ser Pro Thr Asp Leu Gly
                185                 190                 195 gcc atc atc gac agc gtc aac gcg cgc acc ggt gcc gca cgg cca ttc       720
Ala Ile Ile Asp Ser Val Asn Ala Arg Thr Gly Ala Ala Arg Pro Phe
                200                 205                 210 tgg ttc ctg gag gtg atc ggc gcg ccg ggc gag gcg gtg cag ccc agc       768
Trp Phe Leu Glu Val Ile Gly Ala Pro Gly Glu Ala Val Gln Pro Ser
        215                 220                 225 cag tac ttc ggg ctc ggc ggc ggg cag gtc acg gtg acc gag ttc gcc       816
Gln Tyr Phe Gly Leu Gly Gly Gly Gln Val Thr Val Thr Glu Phe Ala
        230                 235                 240 tac ggc aag gag ctc tac ggc aag ttc gcc ggc ggc ggc aag ctg gcc       864
Tyr Gly Lys Glu Leu Tyr Gly Lys Phe Ala Gly Gly Gly Lys Leu Ala
245                 250                 255                 260 gac ctg cag acc ttc ggc ccc agc tgg aac ctg atg ccc agc agc aag       912
Asp Leu Gln Thr Phe Gly Pro Ser Trp Asn Leu Met Pro Ser Ser Lys
                265                 270                 275 gcc atc gct ttc gtc gac aac cac gac aag cag cgc ggc cac ggc ggc       960
Ala Ile Ala Phe Val Asp Asn His Asp Lys Gln Arg Gly His Gly Gly
                280                 285                 290 ggg ggc ggc tac gtc acc tat cac cac ggc agc acc tac gac ctg gcg      1008
Gly Gly Gly Tyr Val Thr Tyr His His Gly Ser Thr Tyr Asp Leu Ala
        295                 300                 305 aac atc ttc atg ctg gcc tgg ccc tat ggc tac ccg gcg ctg atg tca      1056
Asn Ile Phe Met Leu Ala Trp Pro Tyr Gly Tyr Pro Ala Leu Met Ser
310                 315                 320 gct acg gct tca acc agg gca gca gct acg aca cca gct acg gcc cgc      1104
Ala Thr Ala Ser Thr Arg Ala Ala Ala Thr Thr Pro Ala Thr Ala Arg
325                 330                 335                 340 cgc act aca gcg acg gct cga ccc ggg ggc cgt ggg acc gga acc ccg      1152
Arg Thr Thr Ala Thr Ala Arg Pro Gly Gly Arg Gly Thr Gly Thr Pro
                345                 350                 355 cca gcc cgg gtg ctt caa cca gac cgt ggg tgg ctg ggt ctg cga gca      1200
Pro Ala Arg Val Leu Gln Pro Asp Arg Gly Trp Leu Gly Leu Arg Ala
                360                 365                 370
```

|                                                                                                 |      |
|-------------------------------------------------------------------------------------------------|------|
| ccg ctg gcg cgg cat cgg caa cat ggt ggc ctt ccg caa cgc cac cgt                                 | 1248 |
| Pro Leu Ala Arg His Arg Gln His Gly Gly Leu Pro Gln Arg His Arg                                 |      |
|             375             380             385                                                 |      |
| gga caa ctg gtt cgt cag cga ctg gtg gag caa cgg caa caa cca gat                                 | 1296 |
| Gly Gln Leu Val Arg Gln Arg Leu Val Glu Gln Arg Gln Gln Pro Asp                                 |      |
|     390             395             400                                                         |      |
| cgc ctt cgg ccg cgg cga caa ggg ctt cgt cgt cat caa caa gga agg                                 | 1344 |
| Arg Leu Arg Pro Arg Arg Gln Gly Leu Arg Arg His Gln Gln Gly Arg                                 |      |
| 405             410             415             420                                             |      |
| tac ggc gct gac gca gct tcc aga cca gcc tgc cgg ccg gga gta ttg                                 | 1392 |
| Tyr Gly Ala Asp Ala Ala Ser Arg Pro Ala Cys Arg Pro Gly Val Leu                                 |      |
|             425             430             435                                                 |      |
| cga cgt gat ctc cgg cga ctt cgc caa cgg cag ctg cac cgg cac ggt                                 | 1440 |
| Arg Arg Asp Leu Arg Arg Leu Arg Gln Arg Gln Leu His Arg His Gly                                 |      |
|     440             445             450                                                         |      |
| ggt gac cgt gga tgc agg cgg cca cgc gat gct gtc cgc acc cgc tta                                 | 1488 |
| Gly Asp Arg Gly Cys Arg Arg Pro Arg Asp Ala Val Arg Thr Arg Leu                                 |      |
| 455             460             465                                                             |      |
| tgg cgc ggc ggc gat cca cgt cgg tgc gcg cat cgg cga cac gca gca                                 | 1536 |
| Trp Arg Gly Gly Asp Pro Arg Arg Cys Ala His Arg Arg His Ala Ala                                 |      |
|     470             475             480                                                         |      |
| ggt gca gca gtg ctc agc ttg acc ttc aac gag acg gcc gac acc gtg                                 | 1584 |
| Gly Ala Ala Val Leu Ser Leu Thr Phe Asn Glu Thr Ala Asp Thr Val                                 |      |
| 485             490             495             500                                             |      |
| tgg ggc cag aac ctc ttc gtc gtc ggc aac gtc ggc gcg ctc ggc aac                                 | 1632 |
| Trp Gly Gln Asn Leu Phe Val Val Gly Asn Val Gly Ala Leu Gly Asn                                 |      |
|             505             510             515                                                 |      |
| tgg gcg ccc gcg gcc ggg gcg gcg atg acc tgg atc tcc ggc agc ggc                                 | 1680 |
| Trp Ala Pro Ala Ala Gly Ala Ala Met Thr Trp Ile Ser Gly Ser Gly                                 |      |
|     520             525             530                                                         |      |
| agc acc ggc cag tgg cgt gcg acg gtg cag ctg ccc gcc gac acg ccg                                 | 1728 |
| Ser Thr Gly Gln Trp Arg Ala Thr Val Gln Leu Pro Ala Asp Thr Pro                                 |      |
| 535             540             545                                                             |      |
| gtg cag tac aag tac gtg aag aag gac ggc gcc ggc aac gtg gtg tgg                                 | 1776 |
| Val Gln Tyr Lys Tyr Val Lys Lys Asp Gly Ala Gly Asn Val Val Trp                                 |      |
|     550             555             560                                                         |      |
| gaa agc ggc ggc aac cgc gtg gtg acg acg ccc gcg ccc ggg gcg acg                                 | 1824 |
| Glu Ser Gly Gly Asn Arg Val Val Thr Thr Pro Ala Pro Gly Ala Thr                                 |      |
| 565             570             575             580                                             |      |
| atc gcc gtc aac gac agc tgg aag tgacggccgg gggcgccagg acgacaaggc                                | 1878 |
| Ile Ala Val Asn Asp Ser Trp Lys                                                                 |      |
|             585                                                                                 |      |
| cctgagcgcc tcgtacaccg tgcccagcgt ggtggtagtc caactggccc gactggctct                               | 1938 |
| tctggttgct gagcttgcgg ttgtcgcgcg tcactgtggt acc                                                 | 1981 |

<210> SEQ ID NO 8
<211> LENGTH: 1981
<212> TYPE: DNA
<213> ORGANISM: Pseudomonas sp., Strain KO-8940
<220> FEATURE:
<221> NAME/KEY: CDS
<222> LOCATION: (7)..(1848)
<220> FEATURE:
<221> NAME/KEY: mat_peptide
<222> LOCATION: (85)..(1848)
<220> FEATURE:
<223> OTHER INFORMATION: MUTATED GENOMIC DNA
<220> FEATURE:
<223> OTHER INFORMATION: PLASMID: pOS3410L139

<400> SEQUENCE: 8

-continued

| | |
|---|---|
| gaattc atg tcg cgc agg ctg gcg ctg gcc ctg gcc gcc agt gcc gtc<br>       Met Ser Arg Arg Leu Ala Leu Ala Leu Ala Ala Ser Ala Val<br>                -25                 -20                 -15 | 48 |
| ctg gcc ggg ccc tgg gcg gtc ggc gcg gtg cag gcg cag tcc gcg ccg<br>Leu Ala Gly Pro Trp Ala Val Gly Ala Val Gln Ala Gln Ser Ala Pro<br>     -10                -5                   -1  1 | 96 |
| cgc acg gcc ttc gtg cag ctt ttc gag tgg aag tgg acc gac gtc gcc<br>Arg Thr Ala Phe Val Gln Leu Phe Glu Trp Lys Trp Thr Asp Val Ala<br>    5               10                15                20 | 144 |
| cgg gag tgc gag acc tac ctc ggc ccc aag ggt ttc gcg gcc gtg cag<br>Arg Glu Cys Glu Thr Tyr Leu Gly Pro Lys Gly Phe Ala Ala Val Gln<br>              25                  30                  35 | 192 |
| atc tcg ccg ccc aac gag cac aac tgg gtc agc agc ggc gac ggc gcg<br>Ile Ser Pro Pro Asn Glu His Asn Trp Val Ser Ser Gly Asp Gly Ala<br>         40                  45                 50 | 240 |
| ccc tac ccg tgg tgg atg cgc tac cag ccg gtc agc tac agc ctg gac<br>Pro Tyr Pro Trp Trp Met Arg Tyr Gln Pro Val Ser Tyr Ser Leu Asp<br>       55                  60                65 | 288 |
| cgc agc cgc agc ggc act cgc gcc gag ttc cag gac atg gtc aac cgc<br>Arg Ser Arg Ser Gly Thr Arg Ala Glu Phe Gln Asp Met Val Asn Arg<br>  70                75                  80 | 336 |
| tgc aac gca gca ggc gtg ggc atc tac gtc gac gcg gtg atc aac cac<br>Cys Asn Ala Ala Gly Val Gly Ile Tyr Val Asp Ala Val Ile Asn His<br>85                90                  95               100 | 384 |
| atg tcg ggt ggc aac ggc ggc acc tcg agc gca ggg cgc agc tgg agc<br>Met Ser Gly Gly Asn Gly Gly Thr Ser Ser Ala Gly Arg Ser Trp Ser<br>              105               110              115 | 432 |
| cac cac aac tat ccg ggc ctg tac ggc tcg cag gac ttc cat cac ccg<br>His His Asn Tyr Pro Gly Leu Tyr Gly Ser Gln Asp Phe His His Pro<br>         120                125              130 | 480 |
| gtg tgc gcc atc acc aac ctc ggt gac gcg aac aac gtg cag aac tgc<br>Val Cys Ala Ile Thr Asn Leu Gly Asp Ala Asn Asn Val Gln Asn Cys<br>       135                140              145 | 528 |
| gag ctc tcg ggc ctg cag gac ctg aac acc ggc agc agc tac gtg cgc<br>Glu Leu Ser Gly Leu Gln Asp Leu Asn Thr Gly Ser Ser Tyr Val Arg<br>     150                155              160 | 576 |
| ggc aag atc tcc gac tac ctg gtc gac ctg gtc cag atg ggc gtc aag<br>Gly Lys Ile Ser Asp Tyr Leu Val Asp Leu Val Gln Met Gly Val Lys<br>165               170              175              180 | 624 |
| ggc ttg cgc gtc gat gcg gcc aag cac atc agc ccg acg gac ctg ggt<br>Gly Leu Arg Val Asp Ala Ala Lys His Ile Ser Pro Thr Asp Leu Gly<br>         185                190              195 | 672 |
| gcc atc atc gac agc gtc aac gcg cgc acc ggt gcc gca cgg cca ttc<br>Ala Ile Ile Asp Ser Val Asn Ala Arg Thr Gly Ala Ala Arg Pro Phe<br>       200                205              210 | 720 |
| tgg ttc ctg gag gtg atc ggc gcg ccg ggc gag gcg gtg cag ccc agc<br>Trp Phe Leu Glu Val Ile Gly Ala Pro Gly Glu Ala Val Gln Pro Ser<br>     215                220              225 | 768 |
| cag tac ttc ggg ctc ggc ggc ggg cag gtc acg gtg acc gag ttc gcc<br>Gln Tyr Phe Gly Leu Gly Gly Gly Gln Val Thr Val Thr Glu Phe Ala<br>     230                235              240 | 816 |
| tac ggc aag gag ctc tac ggc aag ttc gcc ggc ggc aag ctg gcc<br>Tyr Gly Lys Glu Leu Tyr Gly Lys Phe Ala Gly Gly Lys Leu Ala<br>245             250              255              260 | 864 |
| gac ctg cag acc ttc ggc ccc agc tgg aac ctg atg ccc agc agc aag<br>Asp Leu Gln Thr Phe Gly Pro Ser Trp Asn Leu Met Pro Ser Ser Lys<br>         265                270              275 | 912 |
| gcc atc gct ttc gtc gac aac cac gac aag cag cgc ggc cac ggc ggc<br>Ala Ile Ala Phe Val Asp Asn His Asp Lys Gln Arg Gly His Gly Gly<br>     280                285              290 | 960 |

-continued

```
ggg ggc ggc tac gtc acc tat cac cac ggc agc acc tac gac ctg gcg      1008
Gly Gly Gly Tyr Val Thr Tyr His His Gly Ser Thr Tyr Asp Leu Ala
            295                 300                 305 aac atc ttc atg ctg gcc tgg ccc tat ggc tac ccg gcg ctg atg tca      1056
Asn Ile Phe Met Leu Ala Trp Pro Tyr Gly Tyr Pro Ala Leu Met Ser
310                 315                 320 gct acg gct tca acc agg gca gca gct acg aca cca gct acg gcc cgc      1104
Ala Thr Ala Ser Thr Arg Ala Ala Ala Thr Thr Pro Ala Thr Ala Arg
325                 330                 335                 340 cgc act aca gcg acg gct cga ccc ggg ggc cgt ggg acc gga acc ccg      1152
Arg Thr Thr Ala Thr Ala Arg Pro Gly Gly Arg Gly Thr Gly Thr Pro
            345                 350                 355 cca gcc cgg gtg ctt caa cca gac cgt ggg tgg ctg ggt ctg cga gca      1200
Pro Ala Arg Val Leu Gln Pro Asp Arg Gly Trp Leu Gly Leu Arg Ala
            360                 365                 370 ccg ctg gcg cgg cat cgg caa cat ggt ggc ctt ccg caa cgc cac cgt      1248
Pro Leu Ala Arg His Arg Gln His Gly Gly Leu Pro Gln Arg His Arg
            375                 380                 385 gga caa ctg gtt cgt cag cga ctg gtg gag caa cgg caa caa cca gat      1296
Gly Gln Leu Val Arg Gln Arg Leu Val Glu Gln Arg Gln Gln Pro Asp
390                 395                 400 cgc ctt cgg ccg cgg cga caa ggg ctt cgt cgt cat caa caa gga agg      1344
Arg Leu Arg Pro Arg Arg Gln Gly Leu Arg Arg His Gln Gln Gly Arg
405                 410                 415                 420 tac ggc gct gac gca gct tcc aga cca gcc tgc cgg ccg ggc gta ttg      1392
Tyr Gly Ala Asp Ala Ala Ser Arg Pro Ala Cys Arg Pro Gly Val Leu
            425                 430                 435 cga cgt gat ctc cgg cga ctt cgc caa cgg cag ctg cac cgg cac ggt      1440
Arg Arg Asp Leu Arg Arg Leu Arg Gln Arg Gln Leu His Arg His Gly
            440                 445                 450 ggt gac cgt gga tgc agg cgg cca cgc gat gct gtc cgc acc cgc tta      1488
Gly Asp Arg Gly Cys Arg Arg Pro Arg Asp Ala Val Arg Thr Arg Leu
            455                 460                 465 tgg cgc ggc ggc gat cca cgt cgg tgc gcg cat cgg cga cac gca gca      1536
Trp Arg Gly Gly Asp Pro Arg Arg Cys Ala His Arg Arg His Ala Ala
470                 475                 480 ggt gca gca gtg ctc agc ttg acc ttc aac gag acg gcc gac acc gtg      1584
Gly Ala Ala Val Leu Ser Leu Thr Phe Asn Glu Thr Ala Asp Thr Val
485                 490                 495                 500 tgg ggc cag aac ctc ttc gtc gtc ggc aac gtc ggc gcg ctc ggc aac      1632
Trp Gly Gln Asn Leu Phe Val Val Gly Asn Val Gly Ala Leu Gly Asn
            505                 510                 515 tgg gcg ccc gcg gcc ggg gcg gcg atg acc tgg atc tcc ggc agc ggc      1680
Trp Ala Pro Ala Ala Gly Ala Ala Met Thr Trp Ile Ser Gly Ser Gly
            520                 525                 530 agc acc ggc cag tgg cgt gcg acg gtg cag ctg ccc gcc gac acg ccg      1728
Ser Thr Gly Gln Trp Arg Ala Thr Val Gln Leu Pro Ala Asp Thr Pro
            535                 540                 545 gtg cag tac aag tac gtg aag aag gac ggc gcc ggc aac gtg gtg tgg      1776
Val Gln Tyr Lys Tyr Val Lys Lys Asp Gly Ala Gly Asn Val Val Trp
550                 555                 560 gaa agc ggc ggc aac cgc gtg gtg acg acg ccc gcg ccc ggg gcg acg      1824
Glu Ser Gly Gly Asn Arg Val Val Thr Thr Pro Ala Pro Gly Ala Thr
565                 570                 575                 580 atc gcc gtc aac gac agc tgg aag tgacggccgg gggcgccagg acgacaaggc    1878
Ile Ala Val Asn Asp Ser Trp Lys
                585 cctgagcgcc tcgtacaccg tgcccagcgt ggtggtagtc caactggccc gactggctct   1938
```
tctggttgct gagcttgcgg ttgtcgcgcg tcactgtggt acc                                                        1981

<210> SEQ ID NO 9
<211> LENGTH: 614
<212> TYPE: PRT
<213> ORGANISM: Pseudomonas sp., Strain KO-8940

<400> SEQUENCE: 9

```
Met Ser Arg Arg Leu Ala Leu Ala Leu Ala Ala Ser Ala Val Leu Ala
    -25                 -20                 -15

Gly Pro Trp Ala Val Gly Ala Val Gln Ala Gln Ser Ala Pro Arg Thr
-10                  -5                  -1   1                   5

Ala Phe Val Gln Leu Phe Glu Trp Lys Trp Thr Asp Val Ala Arg Glu
                 10                  15                  20

Cys Glu Thr Tyr Leu Gly Pro Lys Gly Phe Ala Ala Val Gln Ile Ser
             25                  30                  35

Pro Pro Asn Glu His Asn Trp Val Ser Ser Gly Asp Gly Ala Pro Tyr
         40                  45                  50

Pro Trp Phe Met Arg Tyr Gln Pro Val Ser Tyr Ser Leu Asp Arg Ser
55                  60                  65                  70

Arg Ser Gly Thr Arg Ala Glu Phe Gln Asp Met Val Asn Arg Cys Asn
                 75                  80                  85

Ala Ala Gly Val Gly Ile Tyr Val Asp Ala Val Ile Asn His Met Ser
             90                  95                 100

Gly Gly Asn Gly Gly Thr Ser Ser Ala Gly Arg Ser Trp Ser His His
        105                 110                 115

Asn Tyr Pro Gly Leu Tyr Gly Ser Gln Asp Phe His His Pro Val Cys
120                 125                 130

Ala Ile Thr Asn Tyr Gly Asp Ala Asn Asn Val Gln Asn Cys Glu Leu
135                 140                 145                 150

Ser Gly Leu Gln Asp Leu Asn Thr Gly Ser Ser Tyr Val Arg Gly Lys
                155                 160                 165

Ile Ser Asp Tyr Leu Val Asp Leu Val Gln Met Gly Val Lys Gly Leu
            170                 175                 180

Arg Val Asp Ala Ala Lys His Ile Ser Pro Thr Asp Leu Gly Ala Ile
        185                 190                 195

Ile Asp Ser Val Asn Ala Arg Thr Gly Ala Ala Arg Pro Phe Trp Phe
200                 205                 210

Leu Glu Val Ile Gly Ala Pro Gly Glu Ala Val Gln Pro Ser Gln Tyr
215                 220                 225                 230

Phe Gly Leu Gly Gly Gln Val Thr Val Thr Glu Phe Ala Tyr Gly
                235                 240                 245

Lys Glu Leu Tyr Gly Lys Phe Ala Gly Gly Lys Leu Ala Asp Leu
            250                 255                 260

Gln Thr Phe Gly Pro Ser Trp Asn Leu Met Pro Ser Ser Lys Ala Ile
        265                 270                 275

Ala Phe Val Asp Asn His Asp Lys Gln Arg Gly His Gly Gly Gly
280                 285                 290

Gly Tyr Val Thr Tyr His His Gly Ser Thr Tyr Asp Leu Ala Asn Ile
295                 300                 305                 310

Phe Met Leu Ala Trp Pro Tyr Gly Tyr Pro Ala Leu Met Ser Ala Thr
                315                 320                 325

Ala Ser Thr Arg Ala Ala Ala Thr Thr Pro Ala Thr Ala Arg Arg Thr
            330                 335                 340
```

-continued

```
Thr Ala Thr Ala Arg Pro Gly Gly Arg Gly Thr Gly Thr Pro Pro Ala
            345                 350                 355

Arg Val Leu Gln Pro Asp Arg Gly Trp Leu Gly Leu Arg Ala Pro Leu
            360                 365                 370

Ala Arg His Arg Gln His Gly Gly Leu Pro Gln Arg His Arg Gly Gln
375                 380                 385                 390

Leu Val Arg Gln Arg Leu Val Glu Gln Arg Gln Pro Asp Arg Leu
            395                 400                 405

Arg Pro Arg Arg Gln Gly Leu Arg Arg His Gln Gln Gly Arg Tyr Gly
            410                 415                 420

Ala Asp Ala Ala Ser Arg Pro Ala Cys Arg Pro Gly Val Leu Arg Arg
            425                 430                 435

Asp Leu Arg Arg Leu Arg Gln Arg Gln Leu His Arg His Gly Gly Asp
            440                 445                 450

Arg Gly Cys Arg Arg Pro Arg Asp Ala Val Arg Thr Arg Leu Trp Arg
455                 460                 465                 470

Gly Gly Asp Pro Arg Arg Cys Ala His Arg Arg His Ala Ala Gly Ala
            475                 480                 485

Ala Val Leu Ser Leu Thr Phe Asn Glu Thr Ala Asp Thr Val Trp Gly
            490                 495                 500

Gln Asn Leu Phe Val Val Gly Asn Val Gly Ala Leu Gly Asn Trp Ala
            505                 510                 515

Pro Ala Gly Ala Ala Met Thr Trp Ile Ser Gly Ser Gly Ser Thr
            520                 525                 530

Gly Gln Trp Arg Ala Thr Val Gln Leu Pro Ala Asp Thr Pro Val Gln
535                 540                 545                 550

Tyr Lys Tyr Val Lys Lys Asp Gly Ala Gly Asn Val Val Trp Glu Ser
            555                 560                 565

Gly Gly Asn Arg Val Val Thr Pro Ala Pro Gly Ala Thr Ile Ala
            570                 575                 580

Val Asn Asp Ser Trp Lys
            585
```

<210> SEQ ID NO 10
<211> LENGTH: 614
<212> TYPE: PRT
<213> ORGANISM: Pseudomonas sp., Strain KO-8940

<400> SEQUENCE: 10

```
Met Ser Arg Arg Leu Ala Leu Ala Leu Ala Ala Ser Ala Val Leu Ala
            -25                 -20                 -15

Gly Pro Trp Ala Val Gly Ala Val Gln Ala Gln Ser Ala Pro Arg Thr
-10                 -5                  -1  1               5

Ala Phe Val Gln Leu Phe Glu Trp Lys Trp Thr Asp Val Ala Arg Glu
            10                  15                  20

Cys Glu Thr Tyr Leu Gly Pro Lys Gly Phe Ala Ala Val Gln Ile Ser
            25                  30                  35

Pro Pro Asn Glu His Asn Trp Val Ser Ser Gly Asp Gly Ala Pro Tyr
            40                  45                  50

Pro Trp His Met Arg Tyr Gln Pro Val Ser Tyr Ser Leu Asp Arg Ser
55                  60                  65                  70

Arg Ser Gly Thr Arg Ala Glu Phe Gln Asp Met Val Asn Arg Cys Asn
            75                  80                  85

Ala Ala Gly Val Gly Ile Tyr Val Asp Ala Val Ile Asn His Met Ser
            90                  95                  100
```

-continued

```
Gly Gly Asn Gly Gly Thr Ser Ser Ala Gly Arg Ser Trp Ser His His
        105                 110                 115
Asn Tyr Pro Gly Leu Tyr Gly Ser Gln Asp Phe His His Pro Val Cys
        120                 125                 130
Ala Ile Thr Asn Tyr Gly Asp Ala Asn Asn Val Gln Asn Cys Glu Leu
135                 140                 145                 150
Ser Gly Leu Gln Asp Leu Asn Thr Gly Ser Ser Tyr Val Arg Gly Lys
                155                 160                 165
Ile Ser Asp Tyr Leu Val Asp Leu Val Gln Met Gly Val Lys Gly Leu
                170                 175                 180
Arg Val Asp Ala Ala Lys His Ile Ser Pro Thr Asp Leu Gly Ala Ile
                185                 190                 195
Ile Asp Ser Val Asn Ala Arg Thr Gly Ala Ala Arg Pro Phe Trp Phe
200                 205                 210
Leu Glu Val Ile Gly Ala Pro Gly Glu Ala Val Gln Pro Ser Gln Tyr
215                 220                 225                 230
Phe Gly Leu Gly Gly Gln Val Thr Val Thr Glu Phe Ala Tyr Gly
                235                 240                 245
Lys Glu Leu Tyr Gly Lys Phe Ala Gly Gly Lys Leu Ala Asp Leu
                250                 255                 260
Gln Thr Phe Gly Pro Ser Trp Asn Leu Met Pro Ser Ser Lys Ala Ile
                265                 270                 275
Ala Phe Val Asp Asn His Asp Lys Gln Arg Gly His Gly Gly Gly Gly
        280                 285                 290
Gly Tyr Val Thr Tyr His His Gly Ser Thr Tyr Asp Leu Ala Asn Ile
295                 300                 305                 310
Phe Met Leu Ala Trp Pro Tyr Gly Tyr Pro Ala Leu Met Ser Ala Thr
                315                 320                 325
Ala Ser Thr Arg Ala Ala Thr Thr Pro Ala Thr Ala Arg Arg Thr
                330                 335                 340
Thr Ala Thr Ala Arg Pro Gly Gly Arg Gly Thr Gly Thr Pro Pro Ala
                345                 350                 355
Arg Val Leu Gln Pro Asp Arg Gly Trp Leu Gly Leu Arg Ala Pro Leu
        360                 365                 370
Ala Arg His Arg Gln His Gly Gly Leu Pro Gln Arg His Arg Gly Gln
375                 380                 385                 390
Leu Val Arg Gln Arg Leu Val Glu Gln Arg Gln Pro Asp Arg Leu
                395                 400                 405
Arg Pro Arg Arg Gln Gly Leu Arg Arg His Gln Gln Gly Arg Tyr Gly
                410                 415                 420
Ala Asp Ala Ala Ser Arg Pro Ala Cys Arg Pro Gly Val Leu Arg Arg
                425                 430                 435
Asp Leu Arg Arg Leu Arg Gln Arg Leu His Arg His Gly Gly Asp
        440                 445                 450
Arg Gly Cys Arg Arg Pro Arg Asp Ala Val Arg Thr Arg Leu Trp Arg
455                 460                 465                 470
Gly Gly Asp Pro Arg Arg Cys Ala His Arg Arg His Ala Ala Gly Ala
                475                 480                 485
Ala Val Leu Ser Leu Thr Phe Asn Glu Thr Ala Asp Thr Val Trp Gly
                490                 495                 500
Gln Asn Leu Phe Val Val Gly Asn Val Gly Ala Leu Gly Asn Trp Ala
        505                 510                 515
```

-continued

```
Pro Ala Gly Ala Ala Met Thr Trp Ile Ser Gly Ser Thr
    520             525             530
Gly Gln Trp Arg Ala Thr Val Gln Leu Pro Ala Asp Thr Pro Val Gln
535             540             545             550
Tyr Lys Tyr Val Lys Lys Asp Gly Ala Gly Asn Val Val Trp Glu Ser
                555             560             565
Gly Gly Asn Arg Val Val Thr Pro Ala Pro Gly Ala Thr Ile Ala
            570             575             580
Val Asn Asp Ser Trp Lys
            585

<210> SEQ ID NO 11
<211> LENGTH: 614
<212> TYPE: PRT
<213> ORGANISM: Pseudomonas sp., Strain KO-8940

<400> SEQUENCE: 11

Met Ser Arg Arg Leu Ala Leu Ala Leu Ala Ala Ser Ala Val Leu Ala
    -25             -20             -15
Gly Pro Trp Ala Val Gly Ala Val Gln Ala Gln Ser Ala Pro Arg Thr
-10              -5              -1  1               5
Ala Phe Val Gln Leu Phe Glu Trp Lys Trp Thr Asp Val Ala Arg Glu
                10              15              20
Cys Glu Thr Tyr Leu Gly Pro Lys Gly Phe Ala Ala Val Gln Ile Ser
            25              30              35
Pro Pro Asn Glu His Asn Trp Val Ser Ser Gly Asp Gly Ala Pro Tyr
        40              45              50
Pro Trp Leu Met Arg Tyr Gln Pro Val Ser Tyr Ser Leu Asp Arg Ser
55              60              65              70
Arg Ser Gly Thr Arg Ala Glu Phe Gln Asp Met Val Asn Arg Cys Asn
            75              80              85
Ala Ala Gly Val Gly Ile Tyr Val Asp Ala Val Ile Asn His Met Ser
            90              95              100
Gly Gly Asn Gly Gly Thr Ser Ser Ala Gly Arg Ser Trp Ser His His
        105             110             115
Asn Tyr Pro Gly Leu Tyr Gly Ser Gln Asp Phe His His Pro Val Cys
    120             125             130
Ala Ile Thr Asn Tyr Gly Asp Ala Asn Asn Val Gln Asn Cys Glu Leu
135             140             145             150
Ser Gly Leu Gln Asp Leu Asn Thr Gly Ser Ser Tyr Val Arg Gly Lys
                155             160             165
Ile Ser Asp Tyr Leu Val Asp Leu Val Gln Met Gly Val Lys Gly Leu
            170             175             180
Arg Val Asp Ala Ala Lys His Ile Ser Pro Thr Asp Leu Gly Ala Ile
        185             190             195
Ile Asp Ser Val Asn Ala Arg Thr Gly Ala Ala Arg Pro Phe Trp Phe
    200             205             210
Leu Glu Val Ile Gly Ala Pro Gly Glu Ala Val Gln Pro Ser Gln Tyr
215             220             225             230
Phe Gly Leu Gly Gly Gln Val Thr Val Thr Glu Phe Ala Tyr Gly
                235             240             245
Lys Glu Leu Tyr Gly Lys Phe Ala Gly Gly Lys Leu Ala Asp Leu
            250             255             260
Gln Thr Phe Gly Pro Ser Trp Asn Leu Met Pro Ser Ser Lys Ala Ile
        265             270             275
```

```
Ala Phe Val Asp Asn His Asp Lys Gln Arg Gly His Gly Gly Gly
        280                 285                 290

Gly Tyr Val Thr Tyr His His Gly Ser Thr Tyr Asp Leu Ala Asn Ile
295                 300                 305                 310

Phe Met Leu Ala Trp Pro Tyr Gly Tyr Pro Ala Leu Met Ser Ala Thr
                315                 320                 325

Ala Ser Thr Arg Ala Ala Ala Thr Thr Pro Ala Thr Ala Arg Arg Thr
            330                 335                 340

Thr Ala Thr Ala Arg Pro Gly Gly Arg Gly Thr Gly Thr Pro Pro Ala
            345                 350                 355

Arg Val Leu Gln Pro Asp Arg Gly Trp Leu Gly Leu Arg Ala Pro Leu
        360                 365                 370

Ala Arg His Arg Gln His Gly Gly Leu Pro Gln Arg His Arg Gly Gln
375                 380                 385                 390

Leu Val Arg Gln Arg Leu Val Glu Gln Gln Gln Pro Asp Arg Leu
                395                 400                 405

Arg Pro Arg Arg Gln Gly Leu Arg Arg His Gln Gln Gly Arg Tyr Gly
            410                 415                 420

Ala Asp Ala Ala Ser Arg Pro Ala Cys Arg Pro Gly Val Leu Arg Arg
        425                 430                 435

Asp Leu Arg Arg Leu Arg Gln Arg Gln Leu His Arg His Gly Gly Asp
        440                 445                 450

Arg Gly Cys Arg Arg Pro Arg Asp Ala Val Arg Thr Arg Leu Trp Arg
455                 460                 465                 470

Gly Gly Asp Pro Arg Arg Cys Ala His Arg Arg His Ala Ala Gly Ala
                475                 480                 485

Ala Val Leu Ser Leu Thr Phe Asn Glu Thr Ala Asp Thr Val Trp Gly
            490                 495                 500

Gln Asn Leu Phe Val Val Gly Asn Val Gly Ala Leu Gly Asn Trp Ala
        505                 510                 515

Pro Ala Ala Gly Ala Ala Met Thr Trp Ile Ser Gly Ser Gly Ser Thr
    520                 525                 530

Gly Gln Trp Arg Ala Thr Val Gln Leu Pro Ala Asp Thr Pro Val Gln
535                 540                 545                 550

Tyr Lys Tyr Val Lys Lys Asp Gly Ala Gly Asn Val Val Trp Glu Ser
                555                 560                 565

Gly Gly Asn Arg Val Val Thr Pro Ala Pro Gly Ala Thr Ile Ala
            570                 575                 580

Val Asn Asp Ser Trp Lys
        585

<210> SEQ ID NO 12
<211> LENGTH: 614
<212> TYPE: PRT
<213> ORGANISM: Pseudomonas sp., Strain KO-8940

<400> SEQUENCE: 12

Met Ser Arg Arg Leu Ala Leu Ala Leu Ala Ala Ser Ala Val Leu Ala
        -25                 -20                 -15

Gly Pro Trp Ala Val Gly Ala Val Gln Ala Gln Ser Ala Pro Arg Thr
-10                 -5                  -1  1                   5

Ala Phe Val Gln Leu Phe Glu Trp Lys Trp Thr Asp Val Ala Arg Glu
            10                  15                  20
```

```
Cys Glu Thr Tyr Leu Gly Gly Lys Pro Phe Ala Ala Val Gln Ile Ser
         25                  30                  35

Pro Pro Asn Glu His Asn Trp Val Ser Ser Gly Asp Gly Ala Pro Tyr
     40                  45                  50

Pro Trp Trp Met Arg Tyr Gln Pro Val Ser Tyr Ser Leu Asp Arg Ser
 55                  60                  65                  70

Arg Ser Gly Thr Arg Ala Glu Phe Gln Asp Met Val Asn Arg Cys Asn
                 75                  80                  85

Ala Ala Gly Val Gly Ile Tyr Val Asp Ala Val Ile Asn His Met Ser
             90                  95                 100

Gly Gly Asn Gly Gly Thr Ser Ser Ala Gly Arg Ser Trp Ser His His
        105                 110                 115

Asn Tyr Pro Gly Leu Tyr Gly Ser Gln Asp Phe His Pro Val Cys
    120                 125                 130

Ala Ile Thr Asn Phe Gly Asp Ala Asn Asn Val Gln Asn Cys Glu Leu
135                 140                 145                 150

Ser Gly Leu Gln Asp Leu Asn Thr Gly Ser Ser Tyr Val Arg Gly Lys
                155                 160                 165

Ile Ser Asp Tyr Leu Val Asp Leu Val Gln Met Gly Val Lys Gly Leu
                170                 175                 180

Arg Val Asp Ala Ala Lys His Ile Ser Pro Thr Asp Leu Gly Ala Ile
            185                 190                 195

Ile Asp Ser Val Asn Ala Arg Thr Gly Ala Ala Arg Pro Phe Trp Phe
200                 205                 210

Leu Glu Val Ile Gly Ala Pro Gly Glu Ala Val Gln Pro Ser Gln Tyr
215                 220                 225                 230

Phe Gly Leu Gly Gly Gln Val Thr Val Thr Glu Phe Ala Tyr Gly
                235                 240                 245

Lys Glu Leu Tyr Gly Lys Phe Ala Gly Gly Lys Leu Ala Asp Leu
            250                 255                 260

Gln Thr Phe Gly Pro Ser Trp Asn Leu Met Pro Ser Ser Lys Ala Ile
            265                 270                 275

Ala Phe Val Asp Asn His Asp Lys Gln Arg Gly His Gly Gly Gly Gly
    280                 285                 290

Gly Tyr Val Thr Tyr His His Gly Ser Thr Tyr Asp Leu Ala Asn Ile
295                 300                 305                 310

Phe Met Leu Ala Trp Pro Tyr Gly Tyr Pro Ala Leu Met Ser Ala Thr
                315                 320                 325

Ala Ser Thr Arg Ala Ala Ala Thr Thr Pro Ala Thr Ala Arg Arg Thr
            330                 335                 340

Thr Ala Thr Ala Arg Pro Gly Gly Arg Gly Thr Gly Thr Pro Pro Ala
            345                 350                 355

Arg Val Leu Gln Pro Asp Arg Gly Trp Leu Gly Leu Arg Ala Pro Leu
    360                 365                 370

Ala Arg His Arg Gln His Gly Gly Leu Pro Gln Arg His Arg Gly Gln
375                 380                 385                 390

Leu Val Arg Gln Arg Leu Val Glu Arg Gln Gln Pro Asp Arg Leu
                395                 400                 405

Arg Pro Arg Arg Gln Gly Leu Arg His Gln Gln Gly Arg Tyr Gly
            410                 415                 420

Ala Asp Ala Ala Ser Arg Pro Ala Cys Arg Pro Gly Val Leu Arg Arg
            425                 430                 435

Asp Leu Arg Arg Leu Arg Gln Arg Gln Leu His Arg His Gly Gly Asp
```

-continued

```
             440                 445                 450
Arg Gly Cys Arg Arg Pro Arg Asp Ala Val Arg Thr Arg Leu Trp Arg
455                 460                 465                 470

Gly Gly Asp Pro Arg Arg Cys Ala His Arg Arg His Ala Ala Gly Ala
                475                 480                 485

Ala Val Leu Ser Leu Thr Phe Asn Glu Thr Ala Asp Thr Val Trp Gly
                490                 495                 500

Gln Asn Leu Phe Val Val Gly Asn Val Gly Ala Leu Gly Asn Trp Ala
                505                 510                 515

Pro Ala Ala Gly Ala Ala Met Thr Trp Ile Ser Gly Ser Gly Ser Thr
520                 525                 530

Gly Gln Trp Arg Ala Thr Val Gln Leu Pro Ala Asp Thr Pro Val Gln
535                 540                 545                 550

Tyr Lys Tyr Val Lys Lys Asp Gly Ala Gly Asn Val Val Trp Glu Ser
                555                 560                 565

Gly Gly Asn Arg Val Thr Thr Pro Ala Pro Gly Ala Thr Ile Ala
                570                 575                 580

Val Asn Asp Ser Trp Lys
                585

<210> SEQ ID NO 13
<211> LENGTH: 614
<212> TYPE: PRT
<213> ORGANISM: Pseudomonas sp., Strain KO-8940

<400> SEQUENCE: 13

Met Ser Arg Arg Leu Ala Leu Ala Leu Ala Ala Ser Ala Val Leu Ala
        -25                 -20                 -15

Gly Pro Trp Ala Val Gly Ala Val Gln Ala Gln Ser Ala Pro Arg Thr
-10                 -5                  -1   1                5

Ala Phe Val Gln Leu Phe Glu Trp Lys Trp Thr Asp Val Ala Arg Glu
                10                  15                  20

Cys Glu Thr Tyr Leu Gly Pro Lys Gly Phe Ala Ala Val Gln Ile Ser
            25                  30                  35

Pro Pro Asn Glu His Asn Trp Val Ser Ser Gly Asp Gly Ala Pro Tyr
        40                  45                  50

Pro Trp Trp Met Arg Tyr Gln Pro Val Ser Tyr Ser Leu Asp Arg Ser
55                  60                  65                  70

Arg Ser Gly Thr Arg Ala Glu Phe Gln Asp Met Val Asn Arg Cys Asn
                75                  80                  85

Ala Ala Gly Val Gly Ile Tyr Val Asp Ala Val Ile Asn His Met Ser
                90                  95                  100

Gly Gly Asn Gly Gly Thr Ser Ser Ala Gly Arg Ser Trp Ser His His
            105                 110                 115

Asn Tyr Pro Gly Leu Tyr Gly Ser Gln Asp Phe His His Pro Val Cys
        120                 125                 130

Ala Ile Thr Asn His Gly Asp Ala Asn Asn Val Gln Asn Cys Glu Leu
135                 140                 145                 150

Ser Gly Leu Gln Asp Leu Asn Thr Gly Ser Ser Tyr Val Arg Gly Lys
                155                 160                 165

Ile Ser Asp Tyr Leu Val Asp Leu Val Gln Met Gly Val Lys Gly Leu
            170                 175                 180

Arg Val Asp Ala Ala Lys His Ile Ser Pro Thr Asp Leu Gly Ala Ile
        185                 190                 195
```

-continued

```
Ile Asp Ser Val Asn Ala Arg Thr Gly Ala Ala Arg Pro Phe Trp Phe
200                 205                 210

Leu Glu Val Ile Gly Ala Pro Gly Glu Ala Val Gln Pro Ser Gln Tyr
215                 220                 225                 230

Phe Gly Leu Gly Gly Gly Gln Val Thr Val Thr Glu Phe Ala Tyr Gly
            235                 240                 245

Lys Glu Leu Tyr Gly Lys Phe Ala Gly Gly Lys Leu Ala Asp Leu
        250                 255                 260

Gln Thr Phe Gly Pro Ser Trp Asn Leu Met Pro Ser Ser Lys Ala Ile
            265                 270                 275

Ala Phe Val Asp Asn His Asp Lys Gln Arg Gly His Gly Gly Gly
280                 285                 290

Gly Tyr Val Thr Tyr His His Gly Ser Thr Tyr Asp Leu Ala Asn Ile
295                 300                 305                 310

Phe Met Leu Ala Trp Pro Tyr Gly Tyr Pro Ala Leu Met Ser Ala Thr
            315                 320                 325

Ala Ser Thr Arg Ala Ala Ala Thr Thr Pro Ala Thr Ala Arg Arg Thr
            330                 335                 340

Thr Ala Thr Ala Arg Pro Gly Gly Arg Gly Thr Gly Thr Pro Pro Ala
            345                 350                 355

Arg Val Leu Gln Pro Asp Arg Gly Trp Leu Gly Leu Arg Ala Pro Leu
360                 365                 370

Ala Arg His Arg Gln His Gly Gly Leu Pro Gln Arg His Arg Gly Gln
375                 380                 385                 390

Leu Val Arg Gln Arg Leu Val Glu Gln Arg Gln Pro Asp Arg Leu
            395                 400                 405

Arg Pro Arg Arg Gln Gly Leu Arg Arg His Gln Gln Gly Arg Tyr Gly
            410                 415                 420

Ala Asp Ala Ala Ser Arg Pro Ala Cys Arg Pro Gly Val Leu Arg Arg
            425                 430                 435

Asp Leu Arg Arg Leu Arg Gln Arg Gln Leu His Arg His Gly Gly Asp
            440                 445                 450

Arg Gly Cys Arg Arg Pro Arg Asp Ala Val Arg Thr Arg Leu Trp Arg
455                 460                 465                 470

Gly Gly Asp Pro Arg Arg Cys Ala His Arg Arg His Ala Ala Gly Ala
            475                 480                 485

Ala Val Leu Ser Leu Thr Phe Asn Glu Thr Ala Asp Thr Val Trp Gly
            490                 495                 500

Gln Asn Leu Phe Val Val Gly Asn Val Gly Ala Leu Gly Asn Trp Ala
            505                 510                 515

Pro Ala Ala Gly Ala Ala Met Thr Trp Ile Ser Gly Ser Gly Ser Thr
520                 525                 530

Gly Gln Trp Arg Ala Thr Val Gln Leu Pro Ala Asp Thr Pro Val Gln
535                 540                 545                 550

Tyr Lys Tyr Val Lys Lys Asp Gly Ala Gly Asn Val Val Trp Glu Ser
            555                 560                 565

Gly Gly Asn Arg Val Val Thr Thr Pro Ala Pro Gly Ala Thr Ile Ala
            570                 575                 580

Val Asn Asp Ser Trp Lys
            585
```

<210> SEQ ID NO 14
<211> LENGTH: 614
<212> TYPE: PRT

-continued

<213> ORGANISM: Pseudomonas sp., Strain KO-8940

<400> SEQUENCE: 14

Met Ser Arg Arg Leu Ala Leu Ala Ala Ser Ala Val Leu Ala
    -25              -20             -15

Gly Pro Trp Ala Val Gly Ala Val Gln Ala Gln Ser Ala Pro Arg Thr
-10              -5              -1   1              5

Ala Phe Val Gln Leu Phe Glu Trp Lys Trp Thr Asp Val Ala Arg Glu
             10              15              20

Cys Glu Thr Tyr Leu Gly Pro Lys Gly Phe Ala Val Gln Ile Ser
         25              30              35

Pro Pro Asn Glu His Asn Trp Val Ser Ser Gly Asp Gly Ala Pro Tyr
         40              45              50

Pro Trp Trp Met Arg Tyr Gln Pro Val Ser Tyr Ser Leu Asp Arg Ser
55               60              65                           70

Arg Ser Gly Thr Arg Ala Glu Phe Gln Asp Met Val Asn Arg Cys Asn
                 75              80              85

Ala Ala Gly Val Gly Ile Tyr Val Asp Ala Val Ile Asn His Met Ser
             90              95              100

Gly Gly Asn Gly Gly Thr Ser Ser Ala Gly Arg Ser Trp Ser His His
             105             110             115

Asn Tyr Pro Gly Leu Tyr Gly Ser Gln Asp Phe His His Pro Val Cys
         120             125             130

Ala Ile Thr Asn Leu Gly Asp Ala Asn Asn Val Gln Asn Cys Glu Leu
135             140             145             150

Ser Gly Leu Gln Asp Leu Asn Thr Gly Ser Ser Tyr Val Arg Gly Lys
                 155             160             165

Ile Ser Asp Tyr Leu Val Asp Leu Val Gln Met Gly Val Lys Gly Leu
             170             175             180

Arg Val Asp Ala Ala Lys His Ile Ser Pro Thr Asp Leu Gly Ala Ile
             185             190             195

Ile Asp Ser Val Asn Ala Arg Thr Gly Ala Ala Arg Pro Phe Trp Phe
200             205             210

Leu Glu Val Ile Gly Ala Pro Gly Glu Ala Val Gln Pro Ser Gln Tyr
215             220             225             230

Phe Gly Leu Gly Gly Gly Gln Val Thr Val Thr Glu Phe Ala Tyr Gly
             235             240             245

Lys Glu Leu Tyr Gly Lys Phe Ala Gly Gly Lys Leu Ala Asp Leu
             250             255             260

Gln Thr Phe Gly Pro Ser Trp Asn Leu Met Pro Ser Ser Lys Ala Ile
         265             270             275

Ala Phe Val Asp Asn His Asp Lys Gln Arg Gly His Gly Gly Gly Gly
         280             285             290

Gly Tyr Val Thr Tyr His His Gly Ser Thr Tyr Asp Leu Ala Asn Ile
295             300             305             310

Phe Met Leu Ala Trp Pro Tyr Gly Tyr Pro Ala Leu Met Ser Ala Thr
             315             320             325

Ala Ser Thr Arg Ala Ala Ala Thr Thr Pro Ala Thr Ala Arg Arg Thr
             330             335             340

Thr Ala Thr Ala Arg Pro Gly Gly Arg Gly Thr Gly Thr Pro Pro Ala
         345             350             355

Arg Val Leu Gln Pro Asp Arg Gly Trp Leu Gly Leu Arg Ala Pro Leu
360             365             370

```
Ala Arg His Arg Gln His Gly Gly Leu Pro Gln Arg His Arg Gly Gln
375                 380                 385                 390

Leu Val Arg Gln Arg Leu Val Glu Gln Arg Gln Gln Pro Asp Arg Leu
            395                 400                 405

Arg Pro Arg Arg Gln Gly Leu Arg Arg His Gln Gln Gly Arg Tyr Gly
            410                 415                 420

Ala Asp Ala Ala Ser Arg Pro Ala Cys Arg Pro Gly Val Leu Arg Arg
            425                 430                 435

Asp Leu Arg Arg Leu Arg Gln Arg Gln Leu His Arg His Gly Gly Asp
        440                 445                 450

Arg Gly Cys Arg Arg Pro Arg Asp Ala Val Arg Thr Arg Leu Trp Arg
455                 460                 465                 470

Gly Gly Asp Pro Arg Arg Cys Ala His Arg Arg His Ala Ala Gly Ala
                475                 480                 485

Ala Val Leu Ser Leu Thr Phe Asn Glu Thr Ala Asp Thr Val Trp Gly
                490                 495                 500

Gln Asn Leu Phe Val Val Gly Asn Val Gly Ala Leu Gly Asn Trp Ala
            505                 510                 515

Pro Ala Ala Gly Ala Ala Met Thr Trp Ile Ser Gly Ser Gly Ser Thr
    520                 525                 530

Gly Gln Trp Arg Ala Thr Val Gln Leu Pro Ala Asp Thr Pro Val Gln
535                 540                 545                 550

Tyr Lys Tyr Val Lys Lys Asp Gly Ala Gly Asn Val Val Trp Glu Ser
                555                 560                 565

Gly Gly Asn Arg Val Val Thr Thr Pro Ala Pro Gly Ala Thr Ile Ala
            570                 575                 580

Val Asn Asp Ser Trp Lys
            585
```